United States Patent
Smith et al.

(10) Patent No.: US 10,577,335 B2
(45) Date of Patent: *Mar. 3, 2020

(54) ALLYLIC TERMINALLY UNSATURATED HYDROFLUOROAMINE AND ALLYLIC TERMINALLY UNSATURATED HYDROFLUOROETHER COMPOUNDS AND METHODS OF USING THE SAME

(71) Applicant: 3M INNOVATIVE PROPERTIES COMPANY, St. Paul, MN (US)

(72) Inventors: Sean M. Smith, St. Paul, MN (US); Michael J. Bulinski, Stillwater, MN (US); Michael G. Costello, Afton, MN (US); William M. Lamanna, Stillwater, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/770,289

(22) PCT Filed: Nov. 28, 2016

(86) PCT No.: PCT/US2016/063823
§ 371 (c)(1),
(2) Date: Apr. 23, 2018

(87) PCT Pub. No.: WO2017/095732
PCT Pub. Date: Jun. 8, 2017

(65) Prior Publication Data
US 2018/0312478 A1 Nov. 1, 2018

Related U.S. Application Data

(60) Provisional application No. 62/262,200, filed on Dec. 2, 2015.

(51) Int. Cl.
| | |
|---|---|
| C07D 265/30 | (2006.01) |
| C07C 43/17 | (2006.01) |
| C07C 211/24 | (2006.01) |
| C07D 207/10 | (2006.01) |
| C07D 241/04 | (2006.01) |
| C09K 5/10 | (2006.01) |
| H01M 10/0563 | (2010.01) |

(52) U.S. Cl.
CPC ............ *C07D 265/30* (2013.01); *C07C 43/17* (2013.01); *C07C 211/24* (2013.01); *C07D 207/10* (2013.01); *C07D 241/04* (2013.01); *C09K 5/10* (2013.01); *H01M 10/0563* (2013.01); *H01M 2300/002* (2013.01)

(58) Field of Classification Search
None
See application file for complete search history.

(56) References Cited

U.S. PATENT DOCUMENTS

| | | | |
|---|---|---|---|
| 4,782,148 | A | 11/1988 | Abe |
| 4,900,874 | A | 2/1990 | Ihara |
| 4,985,556 | A | 1/1991 | Abe |
| 6,203,944 | B1 | 3/2001 | Turner |
| 6,255,017 | B1 | 7/2001 | Turner |
| 2010/0139274 | A1 | 6/2010 | Zyhowski |
| 2011/0100601 | A1 | 5/2011 | Flynn |
| 2013/0197280 | A1 | 8/2013 | Stepanov |
| 2014/0130713 | A1 | 5/2014 | Costello et al. |

FOREIGN PATENT DOCUMENTS

| | | |
|---|---|---|
| JP | S64-070445 | 3/1989 |
| JP | 2012-123989 | 6/2012 |
| JP | 2014-005419 | 1/2014 |
| WO | WO 03/097588 | 11/2003 |
| WO | WO 2013-086264 | 6/2013 |

(Continued)

OTHER PUBLICATIONS

French et al. Journal of Fluorine Chemistry (2003), 122(1), 63-80.*
Abe, "A New Route to Perfluorovinylamines by the Pyrolytic Reaction of an Alkali Metal Salt of Perfluoro (2-dialkylamino-propionic acids)," Chemistry Letters, 1988, vol. 17, No. 11, pp. 1887-1890.
Abe, "The Electrochemical Fluorination of Nitrogen-Containing Carboxylic Acids. Fluorination of Dimethylamino or Diethylamino Substituted Carboxylic Acid Derivatives," Journal of Fluorine Chemistry, 1990, vol. 48, pp. 257-279.
Abe, "The Electrochemical Fluorination of Nitrogen-Containing Carboxylic Acids. Fluorination of Methyl Esters of Cyclic Amino Group Substituted Carboxylic Acid," Journal of Fluorine Chemistry, 1990, vol. 50, pp. 173-196.

(Continued)

*Primary Examiner* — Ana Z Muresan

(57) ABSTRACT

Described herein is an unsaturated fluorinated compound of formula (I) where X is O or N; Y is F or H; Z is F or CF3; and A is F or CF3 wherein when X is O, then n is 1, Y is H, Z is F, A is F, and Rf is a linear or branched perfluorinated alkyl group comprising 1 to 10 carbon atoms and optionally comprising at least one catenated O or N; and when X is N, then n is 2 and each Rf group are (i) independently selected from a linear or branched perfluorinated alkyl group comprising 1 to 8 carbon atoms and optionally comprising at least one catenated O or N; or (ii) bonded together to form a ring structure comprising 4 to 8 carbon atoms and optionally comprising at least one catenated O or N with the proviso that when Z is $CF_3$ then A is F and when A is $CF_3$ then Z is F and methods of making and using the same.

(I)

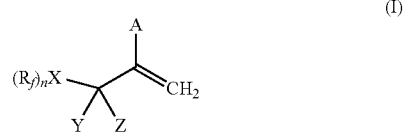

16 Claims, No Drawings

(56) References Cited

FOREIGN PATENT DOCUMENTS

| WO | WO 2015-013155 | 1/2015 |
|----|----------------|--------|
| WO | WO 2016-196240 | 12/2016 |

OTHER PUBLICATIONS

Abe, "An Alternative New Route to Perfluorovinylamines. Pyrolysis of an Alkali Metal Salt of Perfluoro (3-dialkylamino-propionic acids)," Chemistry Letters, 1989, vol. 18, No. 5, pp. 905-908.
Cullen, "Some Reactions of Hexafluorobutyne-2 with Phosphines and Amines," Canadian Journal of Chemistry, 1967, vol. 45, pp. 2887-2894.
Ellis, Cleaning and Contamination of Electronics Components and Assemblies, Electrochemical Publications Limited, Ayr, Scotland, pp. 182-194 (1986).
Gubanov, "Some Reactions of Perfluoromethyl 3,3-Dihydroperfluoroallyl Ether," Zhurnal Obshchei Khimii 1965, vol. 35, pp. 754-755.
Kirij, "Insight into the Reactions of Trifluorovinylsilanes with Aromatic Aldehydes," European Journal of Organic Chemistry, 2008, pp. 2267-2272.
Lebedev, "Pyrolytic Decarboxylation of Some Derivatives of Perfluorinated Mono- and Dicarboxylic Acids", Russian Journal of Applied Chemistry, 2005, vol. 78, No. 10, pp. 1640-1645.
Petrov, "New Partially Fluorinated Epoxides by Oxidation of Olefins with Sodium Hypohalites Under Phase Transfer Catalysis," Journal of Fluorine Chemistry, 2004, vol. 125, pp. 99-105.
International Search Report for PCT International Application No. PCT/US2016/063823, dated Mar. 10, 2017, 3 pages.
Hayakawa et al., "New perfluoropolymers bearing dialkylamino groups as side chains", Polymer, Elsevier Science Publishers B.V, GB, vol. 36, No. 14, Jan. 1, 1995, pp. 2807-2812, XP004025708.

* cited by examiner

ALLYLIC TERMINALLY UNSATURATED HYDROFLUOROAMINE AND ALLYLIC TERMINALLY UNSATURATED HYDROFLUOROETHER COMPOUNDS AND METHODS OF USING THE SAME

CROSS REFERENCE TO RELATED APPLICATIONS

This application is a national stage filing under 35 U.S.C. 371 of PCT/US2016/063823, filed Nov. 28, 2016, which claims the benefit of U.S. Application No. 62/262,200, filed Dec. 2, 2015, the disclosure of which is incorporated by reference in its/their entirety herein.

TECHNICAL FIELD

The present disclosure relates to allylic terminally unsaturated hydrofluorinated compounds comprising an amine and/or ether and methods of making and using the same.

SUMMARY

There continues to be a need for inert fluorinated fluids which have low global warming potential while providing high thermal stability, low toxicity, nonflammability, good solvency, and a wide operating temperature range to meet the requirements of various applications. Those applications include, but are not restricted to, heat transfer, solvent cleaning, fire extinguishing agents, and electrolyte solvents and additives. The fluorinated fluids used in these applications are typically saturated hydrofluoroethers, saturated hydrofluorocarbons, and saturated perfluorocarbons. The fluorinated compounds described herein are unsaturated and comprise an amine and/or ether group. The compounds described herein offer some of the same physical properties as the above-mentioned fluorinated fluids, but generally provide lower atmospheric lifetimes and global warming potentials to provide a more acceptable environmental profile.

In one aspect, an unsaturated fluorinated compound of formula (I) is discussed

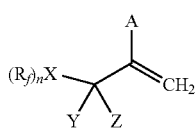

Formula (I)

where X is O or N;
Y is F or H;
Z is F or $CF_3$; and
A is F or $CF_3$
wherein when X is O, then n is 1, Y is H, Z is F, A is F, and $R_f$ is a linear or branched perfluorinated alkyl group comprising 1 to 10 carbon atoms and optionally comprising at least one catenated O or N atom; and
when X is N, then n is 2 and each $R_f$ group is (i) independently selected from a linear or branched perfluorinated alkyl group comprising 1 to 8 carbon atoms and optionally comprising at least one catenated O or N atom; or (ii) bonded together to form a ring structure comprising 4 to 8 carbon atoms and optionally comprising at least one catenated O or N atom with the proviso that when Z is $CF_3$ then A is F and when A is $CF_3$ then Z is F.

The above summary is not intended to describe each embodiment. The details of one or more embodiments of the invention are also set forth in the description below. Other features, objects, and advantages will be apparent from the description and from the claims.

DETAILED DESCRIPTION

As used herein, the term

"a", "an", and "the" are used interchangeably and mean one or more; and

"and/or" is used to indicate one or both stated cases may occur, for example A and/or B includes, (A and B) and (A or B);

"catenated" means an atom other than carbon (for example, oxygen or nitrogen) that is bonded to at least two carbon atoms in a carbon chain (linear or branched or within a ring) so as to form a carbon-heteroatom-carbon linkage;

"perfluorinated" means a group or a compound wherein all hydrogen atoms in the C—H bonds have been replaced by C—F bonds;

"saturated" refers to a compound having no carbon-carbon double bonds or triple bonds;

"unsaturated" refers to a compound having at least one carbon-carbon double bond; and "substituted" (in reference to a group or moiety) means that at least one carbon-bonded hydrogen atom is replaced with a halogen atom. Halogen atoms may include F, Cl, Br, and I.

Also herein, recitation of ranges by endpoints includes all numbers subsumed within that range (e.g., 1 to 10 includes 1.4, 1.9, 2.33, 5.75, 9.98, etc.).

Also herein, recitation of "at least one" includes all numbers of one and greater (e.g., at least 2, at least 4, at least 6, at least 8, at least 10, at least 25, at least 50, at least 100, etc.).

Because of their properties, such as inertness, good solvency, and high thermal stability; fluorinated fluids such as saturated hydrofluoroethers, saturated hydrofluorocarbons, saturated perfluorocarbons, and saturated hydrochlorofluorocarbons have been used in heat transfer, solvent cleaning, fire extinguishing, and electrolyte applications. In view of an increasing demand for environmentally-friendly chemical compounds, it is recognized that there exists an ongoing need for new fluids that provide reductions in environmental impact, and which can meet the performance requirements (e.g., nonflammability, solvency, and operating temperature range) of the traditional fluorinated fluids, while being manufactured cost-effectively.

Generally, the present disclosure provides a new class of hydrofluorinated compounds useful as working fluids. The new compounds are allylic terminally unsaturated hydrofluorinated compounds comprising an amine and/or ether. The compounds of the present disclosure provide similar physical properties to existing fluorinated fluids, but generally exhibit shorter atmospheric lifetimes leading to lower global warming potentials. Typically, saturated perfluorocarbons have atmospheric lifetimes of greater than 2,000 years, saturated hydrofluorocarbons have atmospheric lifetimes of greater than 10 years and saturated hydrofluoroethers have atmospheric lifetimes of from 0.8 to 25 years. In one embodiment, the compounds of the present disclosure have atmospheric lifetimes of less than 1 year, 0.5 years, or even less than 0.1 years.

Surprisingly, in one embodiment, the compounds of the present disclosure can be readily prepared in high yield via low cost starting materials. The starting materials can be readily purchased or derived from electrochemical fluorination. Thus, the compounds described in the present disclosure represent a new class of useful and potentially low cost fluorinated fluid that offer potential advantages in a variety of applications including cleaning, solvent-based coating deposition, heat transfer, foam blowing, fire extinguishing, and battery electrolyte applications.

The unsaturated fluorinated compound of the present disclosure (herein referred to interchangeably as a compound of the present disclosure) are of the general formula (I)

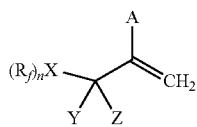

where X is O or N;
Y is F or H;
Z is F or $CF_3$; and
A is F or $CF_3$
wherein when X is O, then n is 1, Y is H, Z is F, A is F, and $R_f$ is a linear or branched perfluorinated alkyl group comprising 1 to 10 (1 to 6, or even 1 to 4) carbon atoms and optionally comprising at least one catenated O or N; and
when X is N, then n is 2 and each $R_f$ group are (i) independently selected from a linear or branched perfluorinated alkyl group comprising 1 to 8 (1 to 6 or even 1 to 3) carbon atoms and optionally comprising at least one catenated O or N; or (ii) bonded together to form a ring structure comprising 4 to 8 carbon atoms and optionally comprising at least one catenated O or N with the proviso that when Z is $CF_3$ then A is F and when A is $CF_3$ then Z is F.

In one embodiment, when X is N, Y is F.
In another embodiment, when X is N, A is F.
In some embodiments, the compound of the present disclosure may have a degree of fluorination that is at least 70%, 75%, 80%, 85% or 90%. In other words, at least 70%, 75%, 80%, 85% or 90% of the C—H bonds in the molecule are replaced by C—F bonds.

Exemplary allylic terminally unsaturated hydrofluorinated amines include:

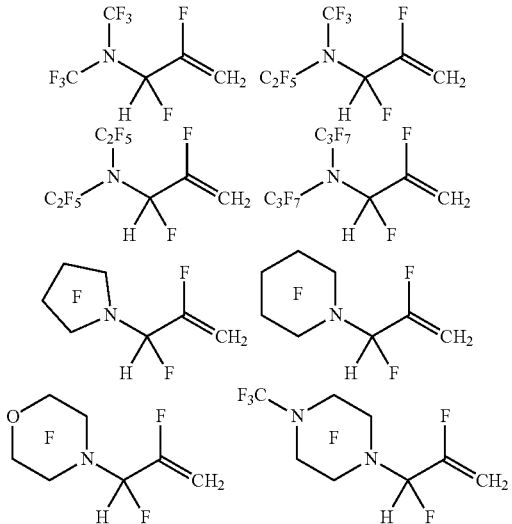

-continued

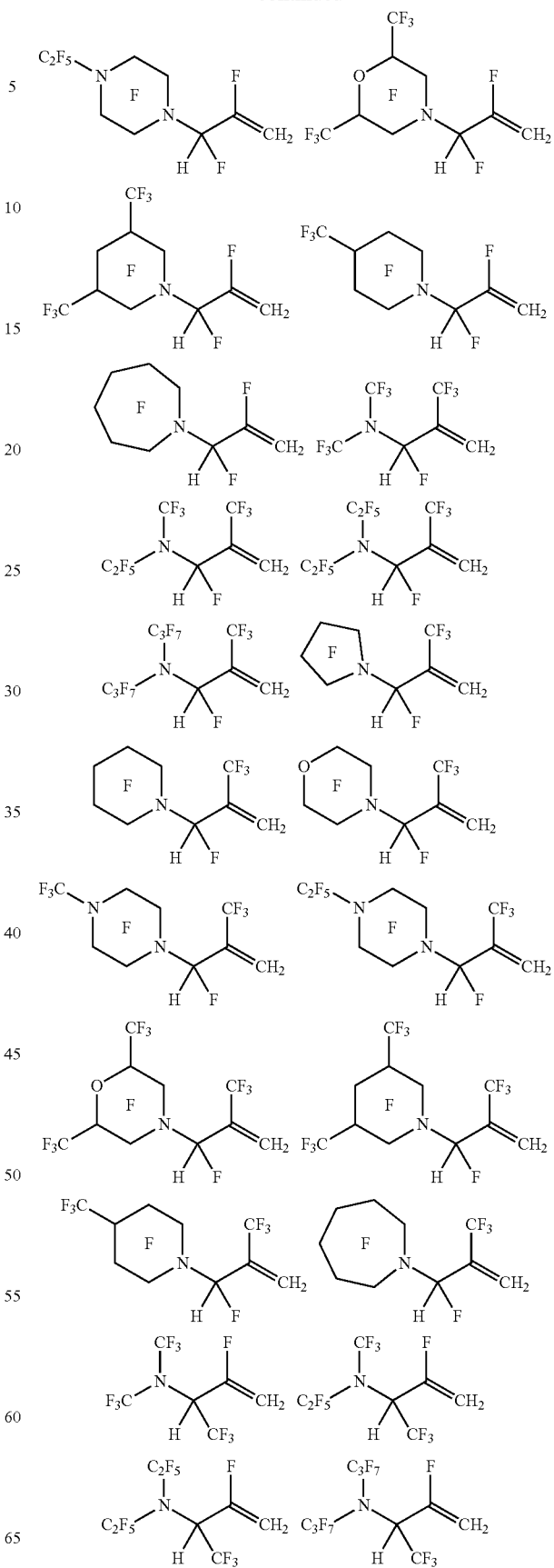

-continued
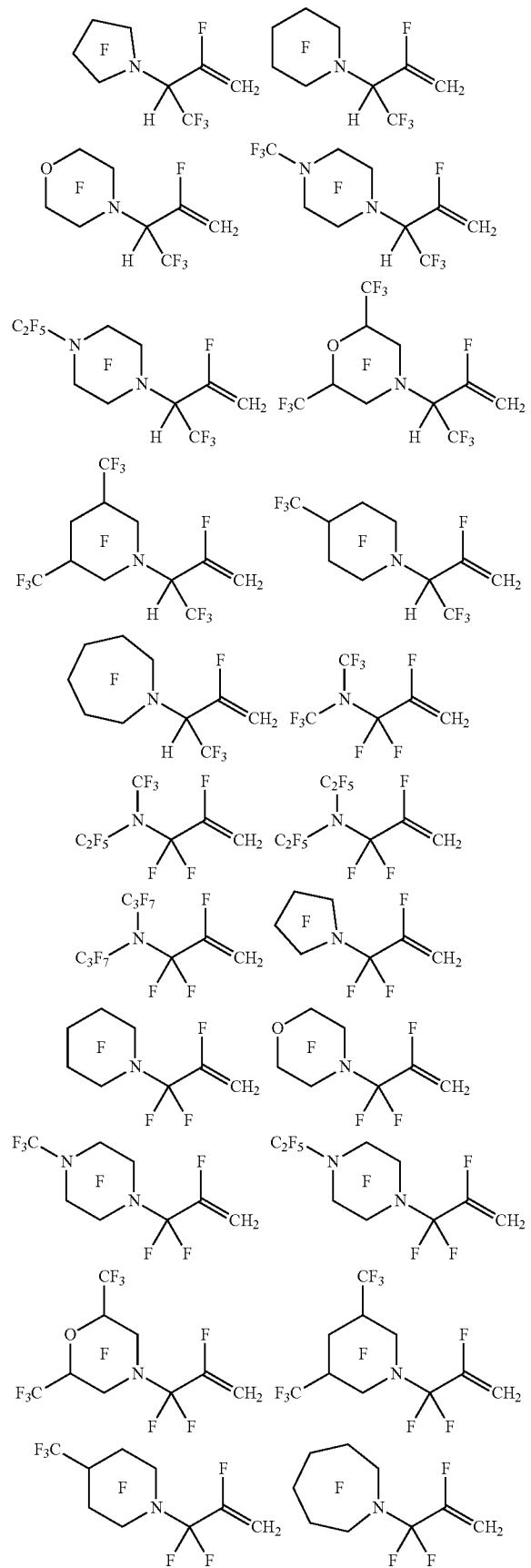
-continued
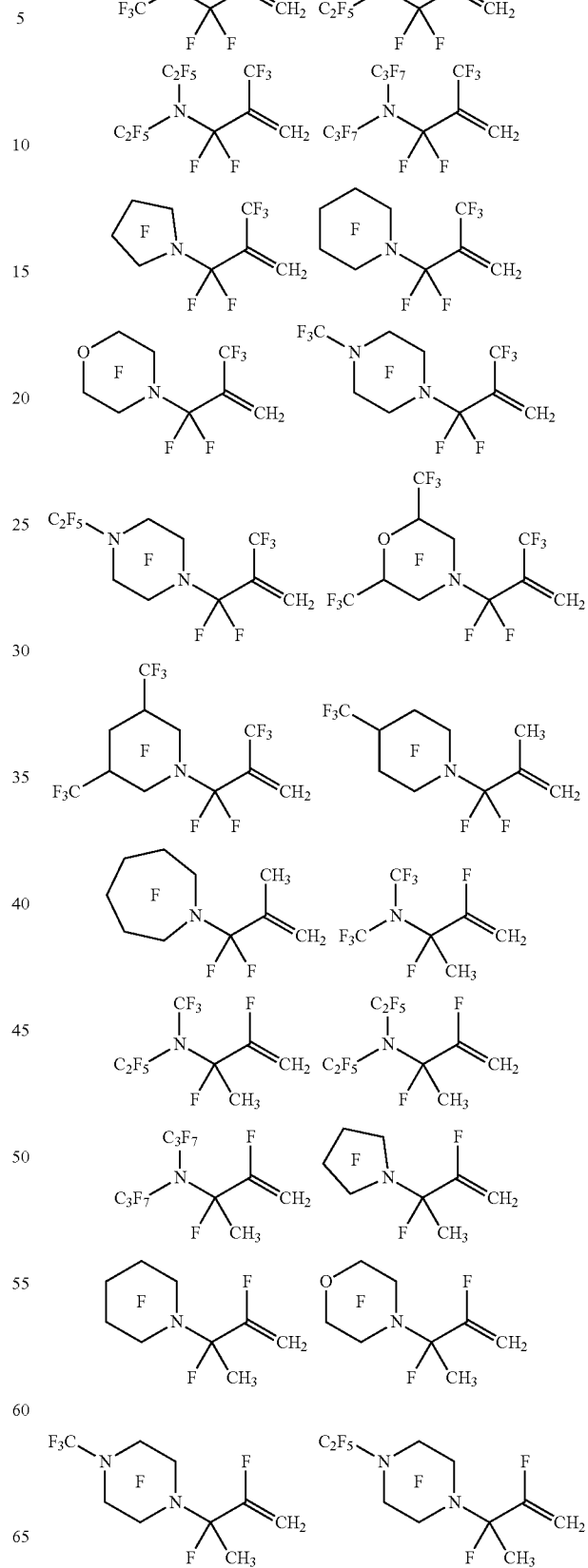

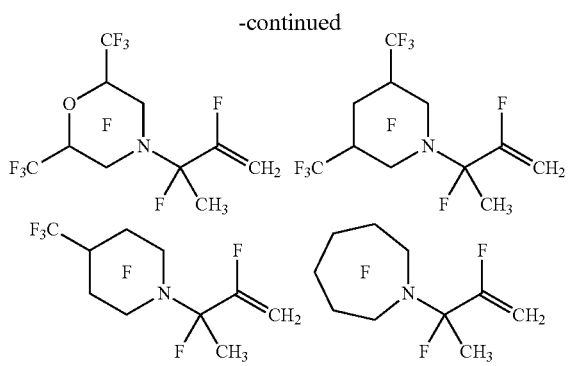

and combinations thereof.

Exemplary allylic terminally unsaturated hydrofluorinated ethers include:

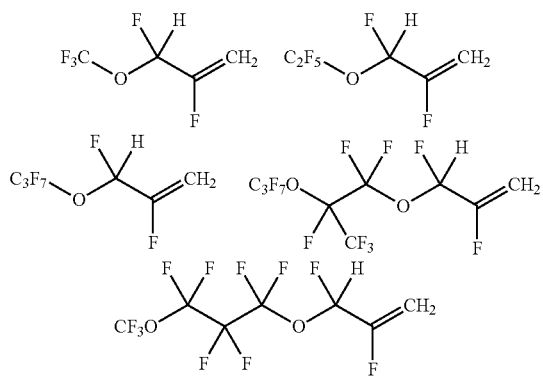

and combinations thereof.

For purposes of the present disclosure, it is to be appreciated that the unsaturated fluorinated compounds disclosed herein may include the E isomer, the Z isomer, or a mixture of the E and Z isomers, irrespective of what is depicted in any of the general formulas or chemical structures.

Non-flammability can be assessed by using standard methods such as ASTM D-3278-96 e-1, D56-05 "Standard Test Method for Flash Point of Liquids by Small Scale Closed-Cup Apparatus". In one embodiment, the compound of the present disclosure is non-flammable based on closed-cup flashpoint testing following ASTM D-327-96 e-1.

In one embodiment, the compound of the present disclosure may have a low environmental impact. In this regard, the compounds of the present disclosure may have a global warming potential (GWP) of less than 100 or even less than 10. As used herein, GWP is a relative measure of the global warming potential of a compound based on the structure of the compound. The GWP of a compound, as defined by the Intergovernmental Panel on Climate Change (IPCC) in 1990 and updated in 2007, is calculated as the warming due to the release of 1 kilogram of a compound relative to the warming due to the release of 1 kilogram of $CO_2$ over a specified integration time horizon (ITH).

$$GWP_i(t') = \frac{\int_0^{ITH} a_i [C(t)] \, dt}{\int_0^{ITH} a_{CO_2} [C_{CO_2}(t)] \, dt} = \frac{\int_0^{ITH} a_i C_{oi} e^{-t/\tau_i} \, dt}{\int_0^{ITH} a_{CO_2} [C_{CO_2}(t)] \, dt}$$

In this equation $a_i$ is the radiative forcing per unit mass increase of a compound in the atmosphere (the change in the flux of radiation through the atmosphere due to the IR absorbance of that compound), C is the atmospheric concentration of a compound, $\tau$ is the atmospheric lifetime of a compound, t is time, and i is the compound of interest. The commonly accepted ITH is 100 years representing a compromise between short-term effects (20 years) and longer-term effects (500 years or longer). The concentration of an organic compound, i, in the atmosphere is assumed to follow pseudo first order kinetics (i.e., exponential decay). The concentration of $CO_2$ over that same time interval incorporates a more complex model for the exchange and removal of $CO_2$ from the atmosphere (the Bern carbon cycle model).

In one embodiment, the compound of the present disclosure is expected to be non-toxic.

In one embodiment, the compound of the present disclosure is non-bioaccumulative in animal tissues. For example, some compounds of the present disclosure may provide low log $K_{ow}$ values, indicating a reduced tendency to bioaccumulate in animal tissues, where $K_{ow}$ is the octanol/water partition coefficient which is defined as the ratio of the given compound's concentration in a two-phase system comprising an octanol phase and an aqueous phase.

In one embodiment, the compound of the present disclosure has a boiling point of at least 60° C., 80° C., 100°, 150° C., or even 200° C.

In some embodiments, the compound of the present disclosure may be hydrophobic, relatively chemically unreactive, and thermally stable.

In some embodiments, the compound of the present disclosure may be prepared by chemical conversion of a fluorinated primary alcohol as shown in the following general reaction Scheme 1:

Scheme 1:

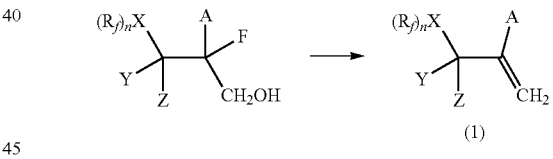

This chemical conversion can be accomplished by a variety of synthetic methods, which are described below.

In one embodiment, the conversion of the fluorinated primary alcohol occurs by contacting the fluorinated primary alcohol with a Lewis acid such as $TiCl_4$ to form a mixture and then diluting the mixture with a solvent followed by contact with a reactive metal in the presence of heat for a sufficient time to form the compounds of the present disclosure, formula (I). Exemplary reactive metals include: magnesium turnings, activated zinc powder, aluminum, and a powder of any of the following metals: magnesium, calcium, titanium, iron, cobalt, nickel, copper, zinc and indium, and also zinc(II) salts. Exemplary solvents include: ether solvent and polar aprotic solvents such as dimethylformamide, dimethylsulfoxide, dimethylacetamide, hexamethylphosphoramide, N-methylpyrolidone, tetrahydrofurane, diglyme, ethyleneglycol dimethyl ether, triglyme, 1,4-dioxane, N-methylepyridine, and mixtures thereof. In yet another embodiment, a solvent is selected from the group consisting of diglyme, diethyl ether, tetrahydrofuran, triglyme, 1,4-dioxane, ethylene glycol dimethyl ether, and mixtures thereof. Such reduction reactions are described in U.S. Pat. Publ. No. 2013/0197280 (Stepanov et al.).

In another embodiment, the conversion of the fluorinated primary alcohol occurs by heating the fluorinated primary alcohol in the presence of hydrogen gas. In one embodiment, a filler may be used to selectively retain the by-products. Exemplary fillers include: activated carbon, silica gel, alumina, zinc oxide, acid clay and potassium fluoride. Such reduction reactions are described in U.S. Pat. No. 4,900,874 (Ihara et al.).

In yet another embodiment, the conversion of the fluorinated primary alcohol occurs by contacting the fluorinated primary alcohol with $SOCl_2$ followed by the addition of a metal fluoride salt (such as NaF, KF, or CsF). Such a chemical reaction is described in Section 3 of "New partially fluorinated epoxides by oxidation of olefins with sodium hypohalites under phase transfer catalysis" by V. A. Petrov, et al., in *Journal of Fluorine Chemistry*, 125 (2004) p. 99-105.

In one embodiment, the starting fluorinated primary alcohols described in Scheme 1 above may be prepared by the reduction of a perfluorinated acid fluoride by hydride reducing agents including, but not limited to, $NaBH_4$, $LiBH_4$, or $LiAlH_4$. These reductions are typically carried out in non-reactive, polar aprotic organic solvents such as tetrahydrofuran, methyl tetrahydrofuran, diethyl ether, methyl tert-butyl ether, cyclopentyl methyl ether, glyme dimethyl ether, diglyme dimethyl ether, triglyme dimethyl ether, and tetraglyme dimethyl ether.

Exemplary amine-containing perfluorinated acid fluorides include:

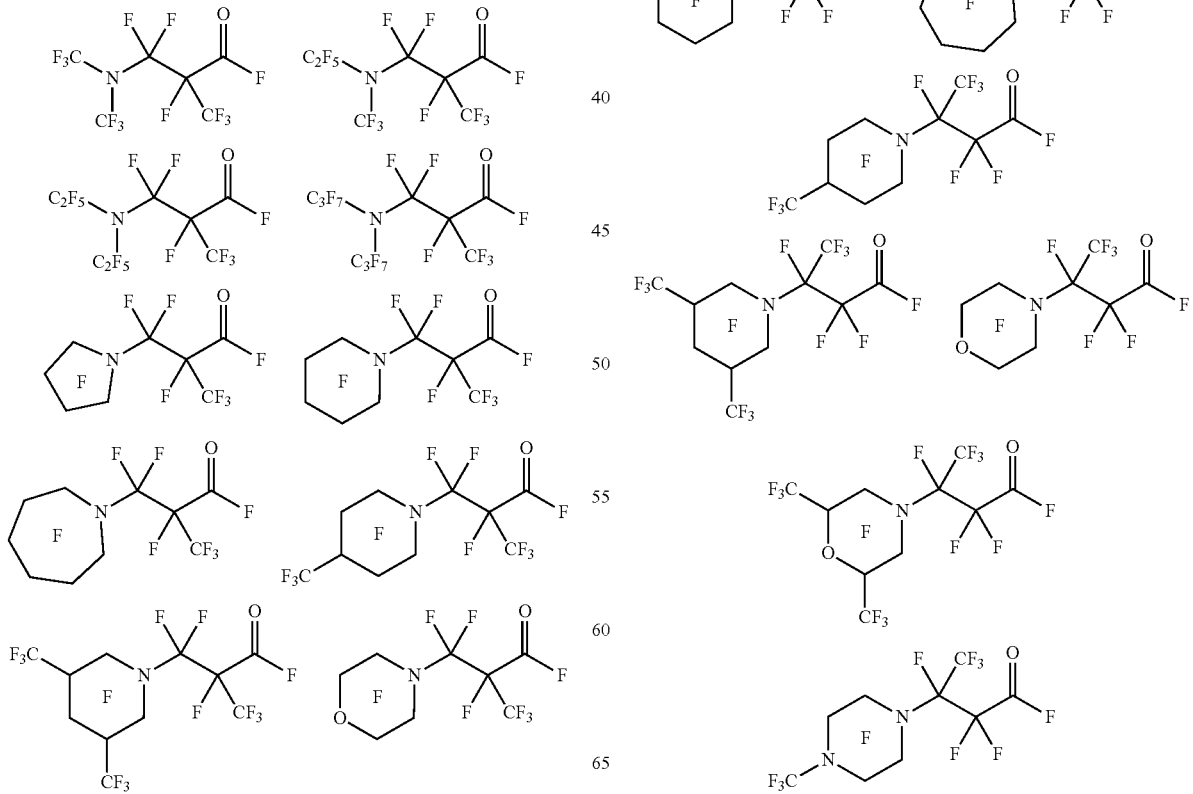

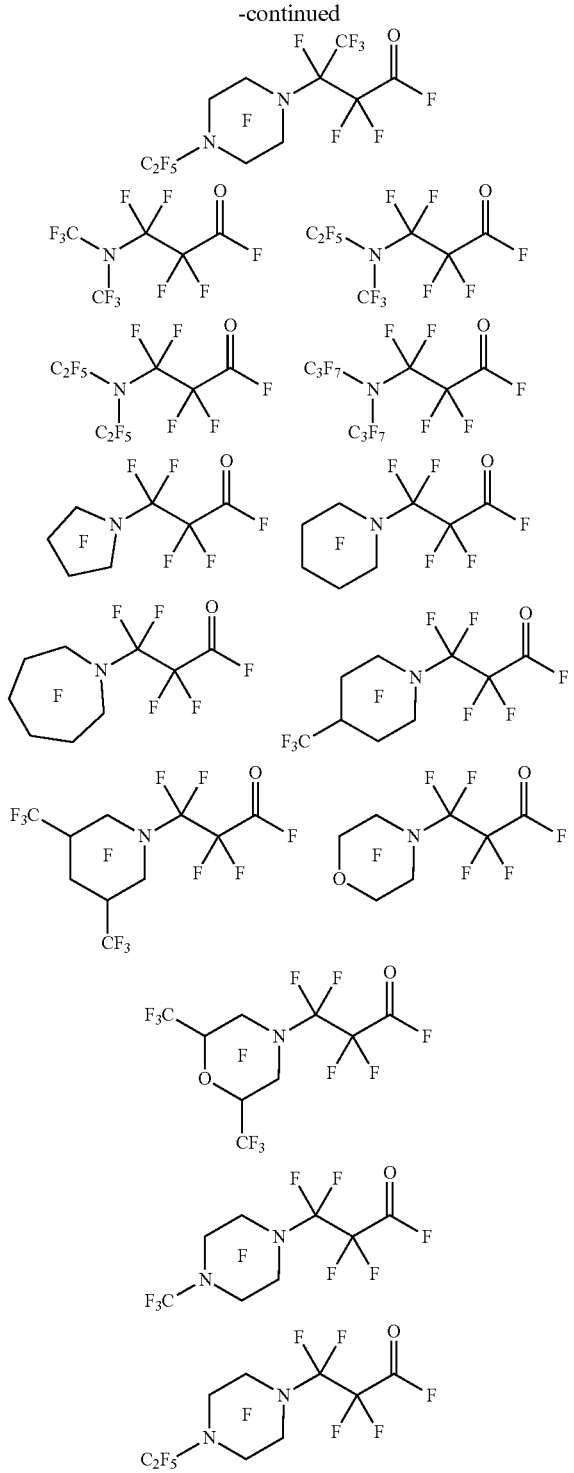

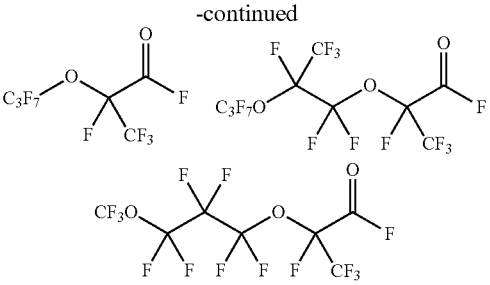

In another embodiment, the starting fluorinated primary alcohols described in Scheme 1 above may be prepared by free radical addition of methanol or trimethyl borate to a perfluorinated vinyl ether, perfluorinated vinyl amine, or perfluorinated propenyl amine. The free radical addition is promoted by suitable free radical initiators including peroxides, peroxyesters, or peroxycarbonates. Examples of such initiators include tert-amylperoxy-2-ethylhexanoate (available under the trade designation "LUPEROX 575" from Arkema, Crosby, Tex.), lauryl peroxide, tert-butyl peroxide, tert-amylperoxy-2-ethylhexyl carbonate, and mixtures thereof, with tert-amylperoxy-2-ethylhexanoate and tert-butyl peroxide being the preferred initiators.

Exemplary perfluorinated vinyl ethers include:

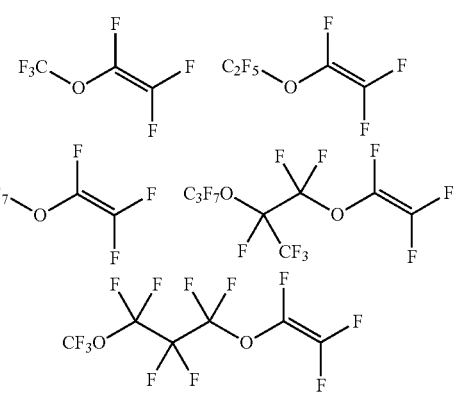

Exemplary perfluorinated vinyl amine and perfluorinated propenyl amines include:

Vinyl amines

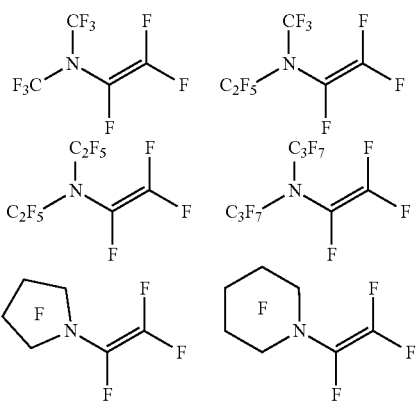

Exemplary ether-containing perfluorinated acid fluorides include:

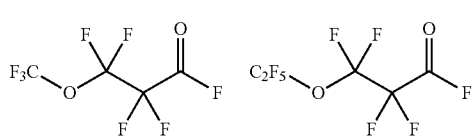

-continued

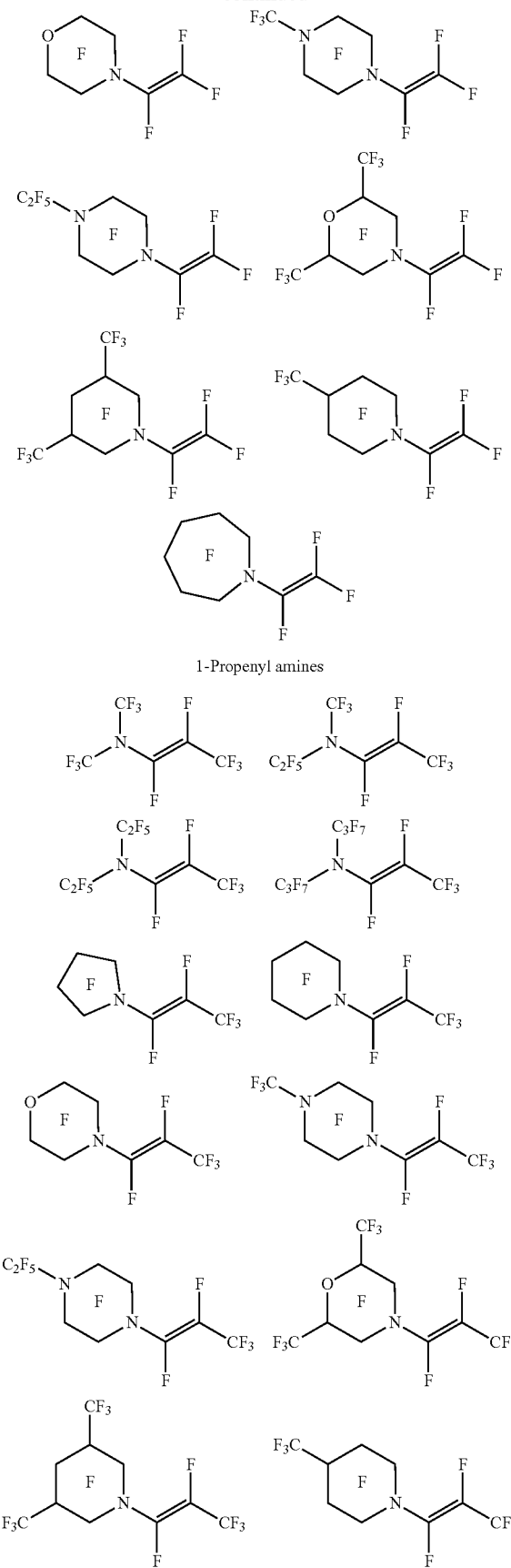

1-Propenyl amines

-continued

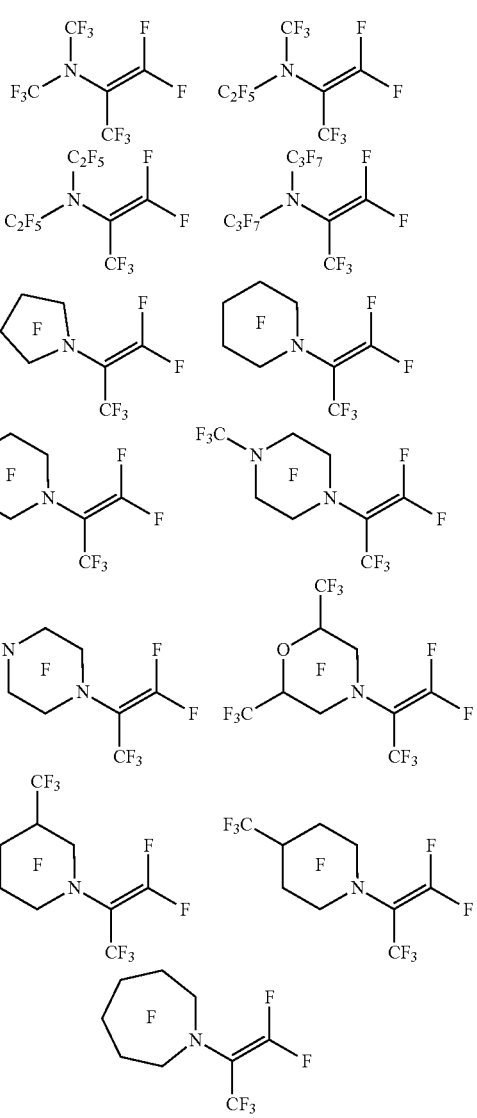

2-Propenyl amines

In some embodiments, the perfluorinated vinyl amine and prefluorinated propenyl amine starting compounds can be prepared by electrochemical perfluorination of the appropriate nitrogen containing hydrocarbon carboxylate derivatives followed by decarboxylation of the perfluorinated nitrogen-containing carboxylates using procedures that are known in the art. Specifically, the perfluorinated acid fluorides, vinyl amines, 1-amino propenes, and 2-amino propenes used in the preparation of compositions of the general formula I, where X=N, can be prepared by synthetic procedures known in the art. See for example, U.S. Pat. No. 4,985,556 (Abe et al.).

An illustrative, low cost route for the preparation of the amine-containing perfluorinated acid fluorides and olefins (including perfluorinated vinyl amines, 1-propenylamines and 2-propenylamines) that are key precursors to compositions of the general formula (I), where X=N, involves the following series of reactions:

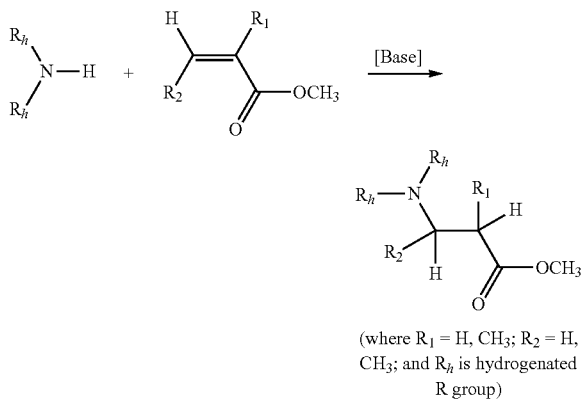

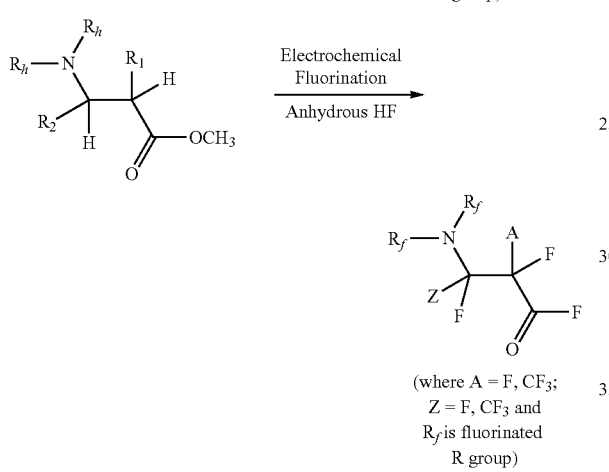

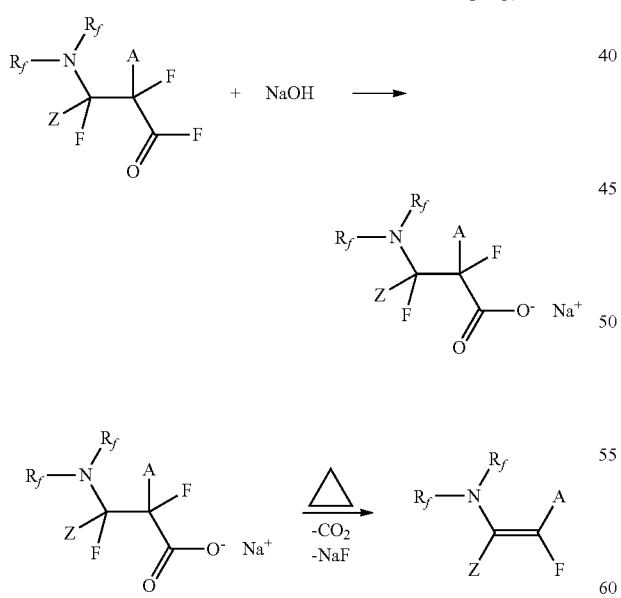

An illustrative, low cost route for the preparation of the ether-containing perfluorinated acid fluorides and perfluorinated vinyl ethers that are key precursors to compositions of the general formula (I), where X=O, involves the following series of reactions:

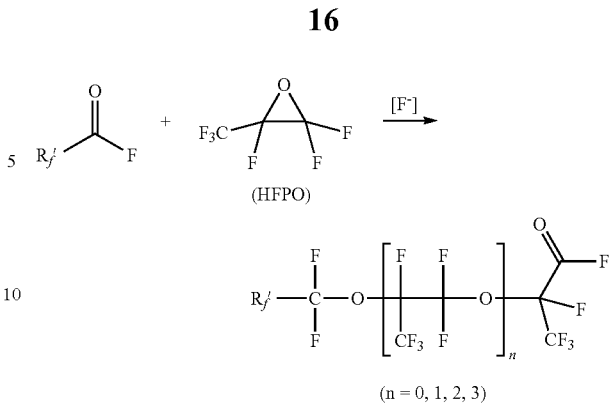

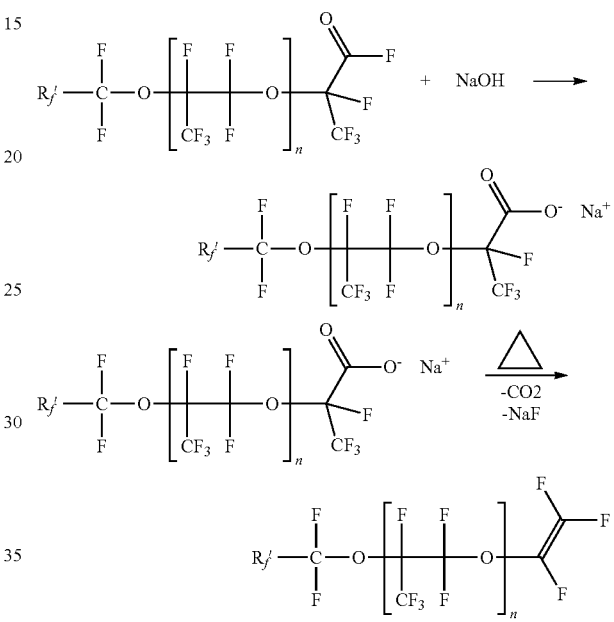

These routes, when combined with the subsequent chemical transformations described herein provide low cost pathways for the commercial production of allylic terminally unsaturated heteroatom-containing hydrofluorocarbons of formula (I).

Thus, the compounds of the present disclosure can be made, for example, by the following two synthetic pathways:

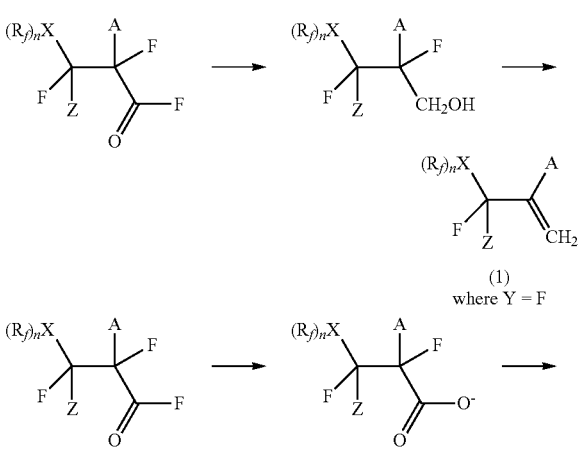

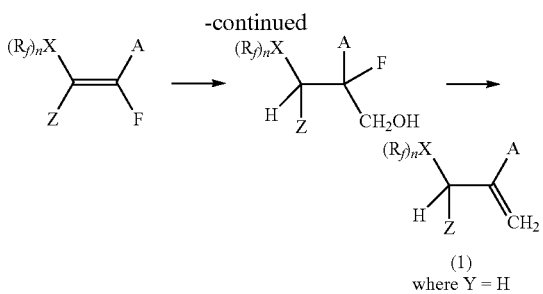

(1)
where Y = H

The compounds of the present disclosure may be used as a working fluid in a variety of applications. The working fluids may include at least 25%, 50%, 70%, 80%, 90%, 95%, 99%, or even 100% by weight of the above-described formula (I) compounds based on the total weight of the working fluid. In addition to the compounds of the present disclosure, the working fluids may include a total of up to 75%, up to 50%, up to 30%, up to 20%, up to 10%, or up to 5% by weight of one or more of the following components: alcohols, ethers, alkanes, alkenes, haloalkenes, perfluorocarbons, perfluorinated tertiary amines, perfluoroethers, cycloalkanes, esters, ketones, oxiranes, aromatics, siloxanes, unsaturated hydrochlorocarbons, unsaturated hydrochlorofluorocarbons, unsaturated hydrofluorocarbons, non-hetero atom-containing hydrofluoroolefins, hydrochloroolefins, hydrochlorofluoroolefins, unsaturated hydrofluoroethers, or mixtures thereof, based on the total weight of the working fluid. Such additional components can be chosen to modify or enhance the properties of a composition for a particular use.

In one embodiment, the working fluid has no flash point (as measured, for example, following ASTM D-3278-96 e-1).

In one embodiment, the compound of the present disclosure is used in a cleaning compositions along with one or more co-solvents. In some embodiments, the present disclosure relates to a process for cleaning a substrate. The cleaning process can be carried out by contacting a contaminated substrate with a cleaning composition. The compound of the present disclosure can be utilized alone or in admixture with each other or with other commonly-used cleaning co-solvents. Representative examples of co-solvents which can be used in the cleaning composition include methanol, ethanol, isopropanol, t-butyl alcohol, methyl t-butyl ether, methyl t-amyl ether, 1,2-dimethoxyethane, cyclohexane, 2,2,4-trimethylpentane, n-decane, terpenes (e.g., a-pinene, camphene, and limonene), trans-1,2-dichloroethylene, cis-1,2-dichloroethylene, methylcyclopentane, decalin, methyl decanoate, t-butyl acetate, ethyl acetate, diethyl phthalate, 2-butanone, methyl isobutyl ketone, naphthalene, toluene, p-chlorobenzotrifluoride, trifluorotoluene, bis(trifluoromethyl)benzenes, hexamethyl disiloxane, octamethyl trisiloxane, perfluorohexane, perfluoroheptane, perfluorooctane, perfluorotributylamine, perfluoro-N-methyl morpholine, perfluoro-2-butyl oxacyclopentane, methylene chloride, chlorocyclohexane, 1-chlorobutane, 1,1-dichloro-1-fluoroethane, 1,1,1-trifluoro-2,2-dichloroethane, 1,1,1,2,2-pentafluoro-3,3-dichloropropane, 1,1,2,2,3-pentafluoro-1,3-dichloropropane, 2,3-dihydroperfluoropentane, 1,1,1,2,2,4-hexafluorobutane, 1-trifluoromethyl-1,2,2-trifluorocyclobutane, 3-methyl-1,1,2,2-tetrafluorocyclobutane, 1-hydropentadecafluoroheptane, or mixtures thereof. Such co-solvents can be chosen to modify or enhance the solvency properties of a cleaning composition for a particular use and can be utilized in ratios (of co-solvent to compounds according to formula (I)) such that the resulting composition has no flash point. If desirable for a particular application, the cleaning composition can further contain one or more dissolved or dispersed gaseous, liquid, or solid additives (for example, carbon dioxide gas, surfactants, stabilizers, antioxidants, or activated carbon).

In some embodiments, the present disclosure relates to cleaning compositions that include one or more compounds of the present disclosure and optionally one or more surfactants. Suitable surfactants include those surfactants that are sufficiently soluble in the compound of the present disclosure, and which promote soil removal by dissolving, dispersing or displacing the soil. One useful class of surfactants are those nonionic surfactants that have a hydrophilic-lipophilic balance (HLB) value of less than about 14. Examples include ethoxylated alcohols, ethoxylated alkylphenols, ethoxylated fatty acids, alkylaryl sulfonates, glycerol esters, ethoxylated fluoroalcohols, and fluorinated sulfonamides. Mixtures of surfactants having complementary properties may be used in which one surfactant is added to the cleaning composition to promote oily soil removal and another added to promote water-soluble soil removal. The surfactant, if used, can be added in an amount sufficient to promote soil removal. Typically, surfactant may be added in amounts from 0.1 to 5.0 wt. % or from 0.2 to 2.0 wt. % of the cleaning composition.

The cleaning compositions can be used in either the gaseous or the liquid state (or both), and any of known or future techniques for "contacting" a substrate can be utilized. For example, a liquid cleaning composition can be sprayed or brushed onto the substrate, a gaseous cleaning composition can be blown across the substrate, or the substrate can be immersed in either a gaseous or a liquid composition. Elevated temperatures, ultrasonic energy, and/or agitation can be used to facilitate the cleaning. Various different solvent cleaning techniques are described by B. N. Ellis in *Cleaning and Contamination of Electronics Components and Assemblies*, Electrochemical Publications Limited, Ayr, Scotland, pages 182-94 (1986).

Both organic and inorganic substrates can be cleaned by the processes of the present disclosure. Representative examples of the substrates include metals; ceramics; glass; polycarbonate; polystyrene; acrylonitrile-butadiene-styrene copolymer; natural fibers (and fabrics derived therefrom) such as cotton, silk, fur, suede, leather, linen, and wool; synthetic fibers (and fabrics) such as polyester, rayon, acrylics, nylon, or blends thereof; fabrics comprising a blend of natural and synthetic fibers; and composites of the foregoing materials. In some embodiments, the process may be used in the precision cleaning of electronic components (e.g., circuit boards), optical or magnetic media, or medical devices.

In one embodiment, the compound of the present disclosure may be used in an apparatus for heat transfer that includes a device and a mechanism for transferring heat to or from the device. The mechanism for transferring heat may include a heat transfer working fluid that includes a compound of formula (I) of the present disclosure.

The provided apparatus for heat transfer may include a device. The device may be a component, work-piece, assembly, etc. to be cooled, heated or maintained at a predetermined temperature or temperature range. Such devices include electrical components, mechanical components and optical components. Examples of devices of the present disclosure include, but are not limited to microprocessors, wafers used to manufacture semiconductor devices, power control semiconductors, electrical distribution switch gear, power transformers, circuit boards, multi-chip modules, packaged and unpackaged semiconductor devices, lasers, chemical reactors, fuel cells, and electrochemical cells. In some embodiments, the device can include a chiller, a heater, or a combination thereof.

In yet other embodiments, the devices can include electronic devices, such as processors, including microprocessors. As these electronic devices become more powerful, the amount of heat generated per unit time increases. Therefore, the mechanism of heat transfer plays an important role in processor performance. The heat-transfer fluid typically has good heat transfer performance, good electrical compatibility (even if used in "indirect contact" applications such as those employing cold plates), as well as low toxicity, low (or non-) flammability and low environmental impact. Good electrical compatibility suggests that the heat-transfer fluid candidate exhibit high dielectric strength, high volume resistivity, and poor solvency for polar materials. Additionally, the heat-transfer fluid should exhibit good mechanical compatibility, that is, it should not affect typical materials of construction in an adverse manner.

The provided apparatus may include a mechanism for transferring heat. The mechanism may include a heat transfer fluid. The heat transfer fluid may include one or more compounds of the present disclosure. Heat may be transferred by placing the heat transfer mechanism in thermal contact with the device. The heat transfer mechanism, when placed in thermal contact with the device, removes heat from the device or provides heat to the device, or maintains the device at a selected temperature or temperature range. The direction of heat flow (from device or to device) is determined by the relative temperature difference between the device and the heat transfer mechanism.

The heat transfer mechanism may include facilities for managing the heat-transfer fluid, including, but not limited to pumps, valves, fluid containment systems, pressure control systems, condensers, heat exchangers, heat sources, heat sinks, refrigeration systems, active temperature control systems, and passive temperature control systems. Examples of suitable heat transfer mechanisms include, but are not limited to, temperature controlled wafer chucks in plasma enhanced chemical vapor deposition (PECVD) tools, temperature-controlled test heads for die performance testing, temperature-controlled work zones within semiconductor process equipment, thermal shock test bath liquid reservoirs, and constant temperature baths. In some systems, such as etchers, ashers, PECVD chambers, vapor phase soldering devices, and thermal shock testers, the upper desired operating temperature may be as high as 170° C., as high as 200° C., or even as high as 230° C.

Heat can be transferred by placing the heat transfer mechanism in thermal contact with the device. The heat transfer mechanism, when placed in thermal contact with the device, removes heat from the device or provides heat to the device, or maintains the device at a selected temperature or temperature range. The direction of heat flow (from device or to device) is determined by the relative temperature difference between the device and the heat transfer mechanism. The provided apparatus can also include refrigeration systems, cooling systems, testing equipment and machining equipment. In some embodiments, the provided apparatus can be a constant temperature bath or a thermal shock test bath.

In another embodiment, the compound of the present disclosure is used as a fire extinguishing composition. The composition may include one or more compounds according to formula (I) and one or more co-extinguishing agents.

In illustrative embodiments, the co-extinguishing agent may include unsaturated hydrofluorocarbons, unsaturated hydrochlorofluorocarbons, unsaturated perfluorocarbons, unsaturated perfluoropolyethers, unsaturated hydrofluoroethers, unsaturated hydrofluoropolyethers, unsaturated chlorofluorocarbons, unsaturated bromofluorocarbons, unsaturated bromochlorofluorocarbons, unsaturated hydrobromocarbons, unsaturated iodofluorocarbons, unsaturated fluorinated ketones, perfluorocarbons, unsaturated hydrobromofluorocarbons, perfluorinated olefins, non-hetero atom-containing hydrofluoroolefins, fluorinated sulfones, fluorinated vinylethers, unsaturated fluoroethers, bromofluoroolefins, chlorofluoroolefins, iodofluoroolefins, fluorinated vinyl amines, fluorinated aminopropenes and mixtures thereof.

Such co-extinguishing agents can be chosen to enhance the extinguishing capabilities or modify the physical properties (e.g., modify the rate of introduction by serving as a propellant) of an extinguishing composition for a particular type (or size or location) of fire and can preferably be utilized in ratios (of co-extinguishing agent to the compound of formula (I)) such that the resulting composition does not form flammable mixtures in air.

In some embodiments, the compounds of formula (I) and the co-extinguishing agent may be present in the fire extinguishing composition in amounts sufficient to suppress or extinguish a fire. The compound of formula (I) and the co-extinguishing agent can be in a weight ratio of from about 9:1 to about 1:9.

In another embodiment, the compound of the present disclosure is used in an apparatus for converting thermal energy into mechanical energy in a Rankine cycle. The apparatus may include a working fluid that includes one or more compounds of formula (I). The apparatus may further include a heat source to vaporize the working fluid and form a vaporized working fluid, a turbine through which the vaporized working fluid is passed thereby converting thermal energy into mechanical energy, a condenser to cool the vaporized working fluid after it is passed through the turbine, and a pump to recirculate the working fluid.

In some embodiments, the present disclosure relates to a process for converting thermal energy into mechanical energy in a Rankine cycle. The process may include using a heat source to vaporize a working fluid that includes one or more compounds of formula (I) to form a vaporized working fluid. In some embodiments, the heat is transferred from the heat source to the working fluid in an evaporator or boiler. The vaporized working fluid may pressurized and can be used to do work by expansion. The heat source can be of any form such as from fossil fuels, e.g., oil, coal, or natural gas. Additionally, in some embodiments, the heat source can come from nuclear power, solar power, or fuel cells. In other embodiments, the heat can be "waste heat" from other heat transfer systems that would otherwise be lost to the atmosphere. The "waste heat," in some embodiments, can be heat that is recovered from a second Rankine cycle system from the condenser or other cooling device in the second Rankine cycle.

An additional source of "waste heat" can be found at landfills where methane gas is flared off. In order to prevent methane gas from entering the environment and thus contributing to global warming, the methane gas generated by the landfills can be burned by way of "flares" producing carbon dioxide and water which are both less harmful to the environment in terms of global warming potential than methane. Other sources of "waste heat" that can be useful in the provided processes are geothermal sources and heat from other types of engines such as gas turbine engines that give off significant heat in their exhaust gases and to cooling liquids such as water and lubricants.

In the provided process, the vaporized working fluid may expanded though a device that can convert the pressurized working fluid into mechanical energy. In some embodiments, the vaporized working fluid is expanded through a turbine which can cause a shaft to rotate from the pressure of the vaporized working fluid expanding. The turbine can then be used to do mechanical work such as, in some embodiments, operate a generator, thus generating electricity. In other embodiments, the turbine can be used to drive belts, wheels, gears, or other devices that can transfer mechanical work or energy for use in attached or linked devices.

After the vaporized working fluid has been converted to mechanical energy the vaporized (and now expanded) working fluid can be condensed using a cooling source to liquefy for reuse. The heat released by the condenser can be used for other purposes including being recycled into the same or another Rankine cycle system, thus saving energy. Finally, the condensed working fluid can be pumped by way of a pump back into the boiler or evaporator for reuse in a closed system.

The desired thermodynamic characteristics of organic Rankine cycle working fluids are well known to those of ordinary skill and are discussed, for example, in U.S. Pat. Appl. Publ. No. 2010/0139274 (Zyhowski et al.). The greater the difference between the temperature of the heat source and the temperature of the condensed liquid or a provided heat sink after condensation, the higher the Rankine cycle thermodynamic efficiency. The thermodynamic efficiency is influenced by matching the working fluid to the heat source temperature. The closer the evaporating temperature of the working fluid to the source temperature, the higher the efficiency of the system. Toluene can be used, for example, in the temperature range of 79° C. to about 260° C., however toluene has toxicological and flammability concerns. Fluids such as 1,1-dichloro-2,2,2-trifluoroethane and 1,1,1,3,3-pentafluoropropane can be used in this temperature range as an alternative. But 1,1-dichloro-2,2,2-trifluoroethane can form toxic compounds below 300° C. and need to be limited to an evaporating temperature of about 93° C. to about 121° C. Thus, there is a desire for other environmentally-friendly Rankine cycle working fluids with higher critical temperatures so that source temperatures such as gas turbine and internal combustion engine exhaust can be better matched to the working fluid.

In yet another embodiment, the compound of the present disclosure is used as nucleating agents in the production of polymeric foams and in particular in the production of polyurethane foams and phenolic foams. In this regard, in some embodiments, the present disclosure is directed to a foamable composition that includes one or more blowing agents, one or more foamable polymers or precursor compositions thereof, and one or more nucleating agents that include a compound of formula (I).

In some embodiments, a variety of blowing agents may be used in the provided foamable compositions including liquid or gaseous blowing agents that are vaporized in order to foam the polymer or gaseous blowing agents that are generated in situ in order to foam the polymer. Illustrative examples of blowing agents include unsaturated hydrochlorofluorocarbons, unsaturated hydrofluorocarbons, unsaturated hydrochlorocarbons, unsaturated iodofluorocarbons, unsaturated hydrocarbons, non-hetero atom-containing hydrofluoroolefins, and unsaturated hydrofluoroethers. The blowing agent for use in the provided foamable compositions can have a boiling point of from about −45° C. to about 100° C. at atmospheric pressure. Typically, at atmospheric pressure the blowing agent has a boiling point of at least about 15° C., more typically between about 20° C. and about 80° C. The blowing agent can have a boiling point of between about 30° C. and about 65° C. Further illustrative examples of blowing agents that can be used in the invention include aliphatic and cycloaliphatic hydrocarbons having about 5 to about 7 carbon atoms, such as n-pentane and cyclopentane, esters such as methyl formate, unsaturated hydrofluorocarbons such as $CF_3CF_2CHFCHFCF_3$, $CF_3CH_2CF_2H$, $CF_3CH_2CF_2CH_3$, $CF_3CF_2H$, $CH_3CF_2H$ (HFC-152a), $CF_3CH_2CH_2CF_3$ and $CHF_2CF_2CH_2F$, unsaturated hydrochlorofluorocarbons such as $CH_3CCl_2F$, $CF_3CHCl_2$, and $CF_2HCl$, unsaturated hydrocarbons such as 2-chloropropane, and unsaturated iodofluorocarbons such as $CF_3I$, and unsaturated hydrofluoroethers such as $C_4F_9OCH_3$ and non-hetero atom-containing hydrofluoroolefin such as $CF_3CF=CH_2$, $CF_3CH=CHF$, $CF_3CH=CHCl$ and $CF_3CH=CHCF_3$. In certain formulations $CO_2$ generated from the reaction of water with foam precursor such as an isocyanate can be used as a blowing agent.

In various embodiments, the provided foamable composition may also include one or more foamable polymers or a precursor composition thereof. Foamable polymers suitable for use in the provided foamable compositions include, for example, polyolefins, e.g., polystyrene, poly(vinyl chloride), and polyethylene. Foams can be prepared from styrene polymers using conventional extrusion methods. The blowing agent composition can be injected into a heat-plastified styrene polymer stream within an extruder and admixed therewith prior to extrusion to form foam. Representative examples of suitable styrene polymers include, for example, the solid homopolymers of styrene, α-methylstyrene, ring-alkylated styrenes, and ring-halogenated styrenes, as well as copolymers of these monomers with minor amounts of other readily copolymerizable olefinic monomers, e.g., methyl methacrylate, acrylonitrile, maleic anhydride, citraconic anhydride, itaconic anhydride, acrylic acid, N-vinylcarbazole, butadiene, and divinylbenzene. Suitable vinyl chloride polymers include, for example, vinyl chloride homopolymer and copolymers of vinyl chloride with other vinyl monomers. Ethylene homopolymers and copolymers of ethylene with, e.g., 2-butene, acrylic acid, propylene, or butadiene may also be useful. Mixtures of different types of polymers can be employed.

In various embodiments, the foamable compositions of the present disclosure may have a molar ratio of nucleating agent to blowing agent of no more than 1:50, 1:25, 1:9, or 1:7, 1:3, or 1:2.

Other conventional components of foam formulations can, optionally, be present in the foamable compositions of the present disclosure. For example, cross-linking or chain-extending agents, foam-stabilizing agents or surfactants, catalysts and fire-retardants can be utilized. Other possible components include fillers (e.g., carbon black), colorants, fungicides, bactericides, antioxidants, reinforcing agents, antistatic agents, and other additives or processing aids.

In some embodiments, polymeric foams can be prepared by vaporizing at least one liquid or gaseous blowing agent or generating at least one gaseous blowing agent in the presence of at least one foamable polymer or a precursor composition thereof and a nucleating agent as described above. In further embodiments, polymeric foams can be prepared using the provided foamable compositions by vaporizing (e.g., by utilizing the heat of precursor reaction)

at least one blowing agent in the presence of a nucleating agent as described above, at least one organic polyisocyanate and at least one compound containing at least two reactive hydrogen atoms. In making a polyisocyanate-based foam, the polyisocyanate, reactive hydrogen-containing compound, and blowing agent composition can generally be combined, thoroughly mixed (using, e.g., any of the various known types of mixing head and spray apparatus), and permitted to expand and cure into a cellular polymer. It is often convenient, but not necessary, to preblend certain of the components of the foamable composition prior to reaction of the polyisocyanate and the reactive hydrogen-containing compound. For example, it is often useful to first blend the reactive hydrogen-containing compound, blowing agent composition, and any other components (e.g., surfactant) except the polyisocyanate, and to then combine the resulting mixture with the polyisocyanate. Alternatively, all components of the foamable composition can be introduced separately. It is also possible to pre-react all or a portion of the reactive hydrogen-containing compound with the polyisocyanate to form a prepolymer.

In still another embodiment, the compound of the present disclosure is used in a dielectric fluids, which can be used in electrical devices (e.g., capacitors, switchgear, transformers, or electric cables or buses). For purposes of the present application, the term "dielectric fluid" is inclusive of both liquid dielectrics and gaseous dielectrics. The physical state of the fluid, gaseous or liquid, is determined at the operating conditions of temperature and pressure of the electrical device in which it is used.

In some embodiments, the dielectric fluids include one or more compounds of formula (I) and, optionally, one or more second dielectric fluids. Suitable second dielectric fluids include, for example, air, nitrogen, helium, argon, and carbon dioxide, or combinations thereof. The second dielectric fluid may be a non-condensable gas or an inert gas. Generally, the second dielectric fluid may be used in amounts such that vapor pressure is at least 70 kPa at 25° C., or at the operating temperature of the electrical device.

The dielectric fluids of the present application comprising the compounds of formula (I) are useful for electrical insulation and for arc quenching and current interruption equipment used in the transmission and distribution of electrical energy. Generally, there are three major types of electrical devices in which the fluids of the present disclosure can be used: (1) gas-insulated circuit breakers and current-interruption equipment, (2) gas-insulated transmission lines, and (3) gas-insulated transformers. Such gas-insulated equipment is a major component of power transmission and distribution systems.

In some embodiments, the present disclosure provides electrical devices, such as capacitors, comprising metal electrodes spaced from each other such that the gaseous dielectric fills the space between the electrodes. The interior space of the electrical device may also comprise a reservoir of the liquid dielectric fluid which is in equilibrium with the gaseous dielectric fluid. Thus, the reservoir may replenish any losses of the dielectric fluid.

In another embodiment, the present disclosure relates to coating compositions comprising (a) a solvent composition that includes one or more compounds of the present disclosure, and (b) one or more coating materials which are soluble or dispersible in the solvent composition.

In various embodiments, the coating materials of the coating compositions may include pigments, lubricants, stabilizers, adhesives, anti-oxidants, dyes, polymers, pharmaceuticals, release agents, inorganic oxides, and the like, and combinations thereof. For example, coating materials may include unsaturated perfluoropolyether, unsaturated hydrocarbon, and silicone lubricants; amorphous copolymers of tetrafluoroethylene; polytetrafluoroethylene; or combinations thereof. Further examples of suitable coating materials include titanium dioxide, iron oxides, magnesium oxide, unsaturated perfluoropolyethers, polysiloxanes, stearic acid, acrylic adhesives, polytetrafluoroethylene, amorphous copolymers of tetrafluoroethylene, or combinations thereof.

In some embodiments, the above-described coating compositions can be useful in coating deposition, where the compounds of Formula (I) function as a carrier for a coating material to enable deposition of the material on the surface of a substrate. In this regard, the present disclosure further relates to a process for depositing a coating on a substrate surface using the coating composition. The process comprises the step of applying to at least a portion of at least one surface of a substrate a coating of a liquid coating composition comprising (a) a solvent composition containing one or more of the compounds of formula (I); and (b) one or more coating materials which are soluble or dispersible in the solvent composition. The solvent composition can further comprise one or more co-dispersants or co-solvents and/or one or more additives (e.g., surfactants, coloring agents, stabilizers, anti-oxidants, flame retardants, and the like). Preferably, the process further comprises the step of removing the solvent composition from the coating by, e.g., allowing evaporation (which can be aided by the application of, e.g., heat or vacuum).

In various embodiments, to form a coating composition, the components of the coating composition (i.e., the compound(s) of formula (I), the coating material(s), and any co-dispersant(s) or co-solvent(s) utilized) can be combined by any conventional mixing technique used for dissolving, dispersing, or emulsifying coating materials, e.g., by mechanical agitation, ultrasonic agitation, manual agitation, and the like. The solvent composition and the coating material(s) can be combined in any ratio depending upon the desired thickness of the coating. For example, the coating material(s) may constitute from about 0.1 to about 10 weight percent of the coating composition.

In illustrative embodiments, the deposition process of the disclosure can be carried out by applying the coating composition to a substrate by any conventional technique. For example, the composition can be brushed or sprayed (e.g., as an aerosol) onto the substrate, or the substrate can be spin-coated. In some embodiments, the substrate may be coated by immersion in the composition. Immersion can be carried out at any suitable temperature and can be maintained for any convenient length of time. If the substrate is a tubing, such as a catheter, and it is desired to ensure that the composition coats the lumen wall, the composition may be drawn into the lumen by the application of reduced pressure.

In various embodiments, after a coating is applied to a substrate, the solvent composition can be removed from the coating (e.g., by evaporation). If desired, the rate of evaporation can be accelerated by application of reduced pressure or mild heat. The coating can be of any convenient thickness, and, in practice, the thickness will be determined by such factors as the viscosity of the coating material, the temperature at which the coating is applied, and the rate of withdrawal (if immersion is utilized).

Both organic and inorganic substrates can be coated by the processes of the present disclosure. Representative examples of the substrates include metals, ceramics, glass, polycarbonate, polystyrene, acrylonitrile-butadiene-styrene copolymer, natural fibers (and fabrics derived therefrom) such as cotton, silk, fur, suede, leather, linen, and wool, synthetic fibers (and fabrics) such as polyester, rayon, acrylics, nylon, or blends thereof, fabrics including a blend of natural and synthetic fibers, and composites of the foregoing materials. In some embodiments, substrates that may be coated include, for example, magnetic hard disks or electrical connectors with perfluoropolyether lubricants or medical devices with silicone lubricants.

In some embodiments, the present disclosure further relates to electrolyte compositions that include one or more compounds of the present disclosure. The electrolyte compositions may comprise (a) a solvent composition including one or more of the compounds according to formula (I); and (b) at least one electrolyte salt. The electrolyte compositions of the present disclosure exhibit excellent oxidative stability, and when used in high voltage electrochemical cells (such as rechargeable lithium ion batteries) provide outstanding cycle life and calendar life. For example, when such electrolyte compositions are used in an electrochemical cell with a graphitized carbon electrode, the electrolytes provide stable cycling to a maximum charge voltage of at least 4.5V and up to 6.0V vs. Li/Li$^+$.

Electrolyte salts that are suitable for use in preparing the electrolyte compositions of the present disclosure include those salts that comprise at least one cation and at least one weakly coordinating anion (the conjugate acid of the anion having an acidity greater than or equal to that of a hydrocarbon sulfonic acid (for example, a bis(perfluoroalkanesulfonyl)imide anion); that are at least partially soluble in a selected compound of formula (I) (or in a blend thereof with one or more other compounds of formula (I) or one or more conventional electrolyte solvents); and that at least partially dissociate to form a conductive electrolyte composition. The salts may be stable over a range of operating voltages, are non-corrosive, and are thermally and hydrolytically stable. Suitable cations include alkali metal, alkaline earth metal, Group IIB metal, Group IIIB metal, transition metal, rare earth metal, and ammonium (for example, tetraalkylammonium or trialkylammonium) cations, as well as a proton. In some embodiments, cations for battery use include alkali metal and alkaline earth metal cations. Suitable anions include fluorine-containing inorganic anions such as $(FSO_2)_2N^-$, $BF_4^-$, $PF_6^-$, $AsF_6^-$, and $SbF_6^-$; $ClO_4^-$; $HSO_4^-$; $H_2PO_4^-$; organic anions such as alkane, aryl, and alkaryl sulfonates; fluorine-containing and nonfluorinated tetraarylborates; carboranes and halogen-, alkyl-, or haloalkylsubstituted carborane anions including metallocarborane anions; and fluorine-containing organic anions such as perfluoroalkanesulfonates, cyanoperfluoroalkanesulfonylamides, bis(cyano)perfluoroalkanesulfonylmethides, (perfluoroalkanesulfonyl)imides, bis(perfluoroalkanesulfonyl) methides, and tris(perfluoroalkanesulfonyl)methides; and the like. Preferred anions for battery use include fluorine-containing inorganic anions (for example, $(FSO_2)_2N^-$, $BF_4^-$, $PF_6^-$, and $AsF_6^-$) and fluorine-containing organic anions (for example, perfluoroalkanesulfonates, bis(perfluoroalkanesulfonyl)imides, and tris(perfluoroalkanesulfonyl)methides). The fluorine-containing organic anions can be either fully fluorinated, that is perfluorinated, or partially fluorinated (within the organic portion thereof). In some embodiments, the fluorine-containing organic anion is at least about 80 percent fluorinated (that is, at least about 80 percent of the carbon-bonded substituents of the anion are fluorine atoms). In some embodiments, the anion is perfluorinated. The anions, including the perfluorinated anions, can contain one or more catenary heteroatoms such as, for example, nitrogen, oxygen, or sulfur. In some embodiments, fluorine-containing organic anions include perfluoroalkanesulfonates, bis(perfluoroalkanesulfonyl)imides, and tris (perfluoroalkanesulfonyl)methides.

In some embodiments, the electrolyte salts may include lithium salts. Suitable lithium salts include, for example, lithium hexafluorophosphate, lithium bis(trifluoromethanesulfonyl)imide, lithium bis(perfluoroethanesulfonyl)imide, lithium tetrafluoroborate, lithium perchlorate, lithium hexafluoroarsenate, lithium trifluoromethanesulfonate, lithium tris(trifluoromethanesulfonyl)methide, lithium bis (fluorosulfonyl)imide (Li-FSI), and mixtures of two or more thereof.

The electrolyte compositions of the present disclosure can be prepared by combining at least one electrolyte salt and a solvent composition including at least one compound of formula (I), such that the salt is at least partially dissolved in the solvent composition at the desired operating temperature. The compounds of the present disclosure (or a normally liquid composition including, consisting, or consisting essentially thereof) can be used in such preparation.

In some embodiments, the electrolyte salt is employed in the electrolyte composition at a concentration such that the conductivity of the electrolyte composition is at or near its maximum value (typically, for example, at a Li molar concentration of around 0.1-4.0 M, or 1.0-2.0 M, for electrolytes for lithium batteries), although a wide range of other concentrations may also be employed.

In some embodiments, one or more conventional electrolyte solvents are mixed with the compound(s) of formula (I) (for example, such that the compound(s) of formula (I) constitute from about 1 to about 80 or 90 percent of the resulting solvent composition). Useful conventional electrolyte solvents include, for example, organic and fluorine-containing electrolyte solvents (for example, propylene carbonate, ethylene carbonate, dimethyl carbonate, diethyl carbonate, ethyl methyl carbonate, dimethoxyethane, γ-butyrolactone, diglyme (that is, diethylene glycol dimethyl ether), tetraglyme (that is, tetraethylene glycol dimethyl ether), monofluoroethylene carbonate, vinylene carbonate, ethyl acetate, methyl butyrate, tetrahydrofuran, alkyl-substituted tetrahydrofuran, 1,3-dioxolane, alkyl-substituted 1,3-dioxolane, tetrahydropyran, alkyl-substituted tetrahydropyran, and the like, and mixtures thereof). Other conventional electrolyte additives (for example, a surfactant) can also be present, if desired.

The present disclosure further relates to electrochemical cells (e.g., fuel cells, batteries, capacitors, electrochromic windows) that include the above-described electrolyte compositions. Such an electrochemical cell may include a positive electrode, a negative electrode, a separator, and the above-described electrolyte composition.

A variety of negative and positive electrodes may be employed in the electrochemical cells. Representative negative electrodes include graphitic carbons e. g., those having a spacing between (002) crystallographic planes, $d_{002}$, of 3.45 Å>$d_{002}$>3.354 Å and existing in forms such as powders, flakes, fibers or spheres (e. g., mesocarbon microbeads); $Li_{4/3}Ti_{5/3}O_4$ the lithium alloy compositions described in U.S. Pat. No. 6,203,944 (Turner et al.) and U.S. Pat. No. 6,255, 017 (Turner); and combinations thereof. Representative positive electrodes include $LiFePO_4$, $LiMnPO_4$, $LiCoPO_4$, $LiMn_2O_4$, $LiCoO_2$ and combinations thereof. The negative or positive electrode may contain additives such as will be familiar to those skilled in the art, e. g., carbon black for negative electrodes and carbon black, flake graphite and the like for positive electrodes.

The electrochemical devices of the invention can be used in various electronic articles such as computers, power tools, automobiles, telecommunication devices, and the like.

Exemplary embodiments of the present disclosure include:

Embodiment 1

An unsaturated fluorinated compound of formula (I)

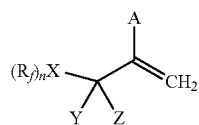

where X is O or N;
Y is F or H;
Z is F or $CF_3$; and
A is F or $CF_3$
wherein when X is O, then n is 1, Y is H, Z is F, A is F, and $R_f$ is a linear or branched perfluorinated alkyl group comprising 1 to 10 carbon atoms and optionally comprising at least one catenated O or N atom; and
when X is N, then n is 2 and each $R_f$ group are (i) independently selected from a linear or branched perfluorinated alkyl group comprising 1 to 8 carbon atoms and optionally comprising at least one catenated O or N atom; or (ii) bonded together to form a ring structure comprising 4 to 8 carbon atoms and optionally comprising at least one catenated O or N atom with the proviso that when Z is $CF_3$ then A is F and when A is $CF_3$ then Z is F.

Embodiment 2

The unsaturated fluorinated compound of embodiment 1, wherein when X is N, Y is F.

Embodiment 3

The unsaturated fluorinated compound of embodiment 1, wherein when X is N, A is F.

Embodiment 4

The unsaturated fluorinated compound of embodiment 1, wherein the unsaturated fluorinated compound has a % fluorine content of 75%.

Embodiment 5

The unsaturated fluorinated compound of embodiment 1, wherein the unsaturated fluorinated compound comprises at least one of the following:

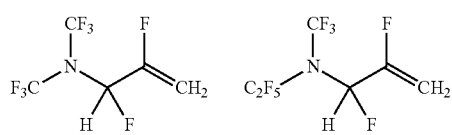

-continued

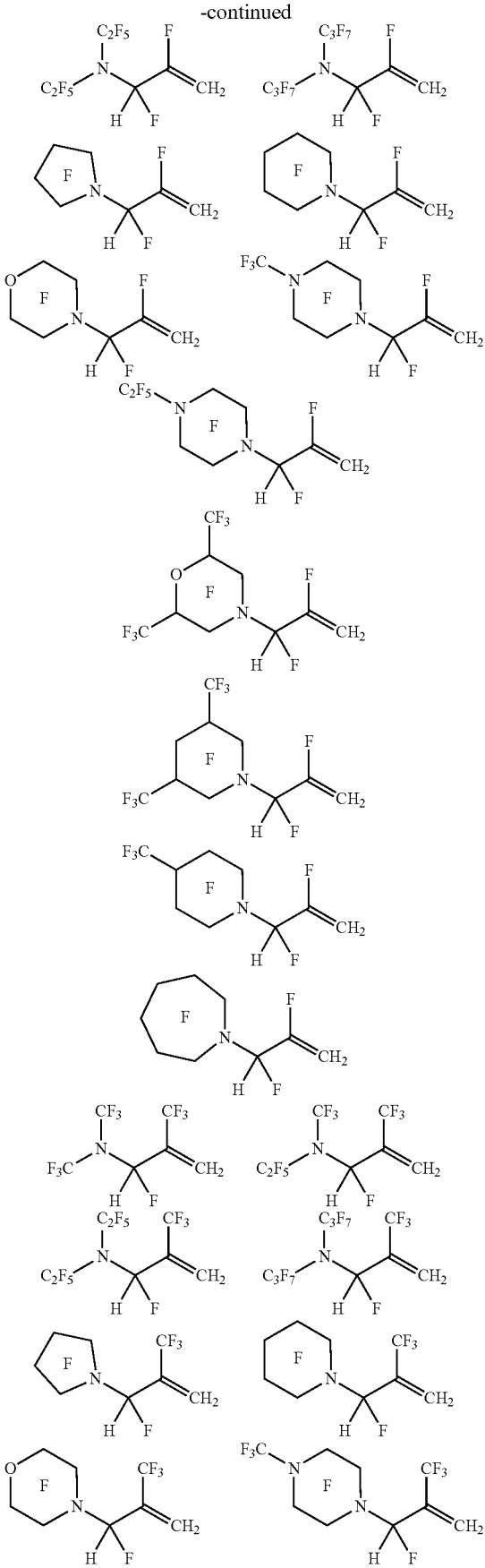

-continued
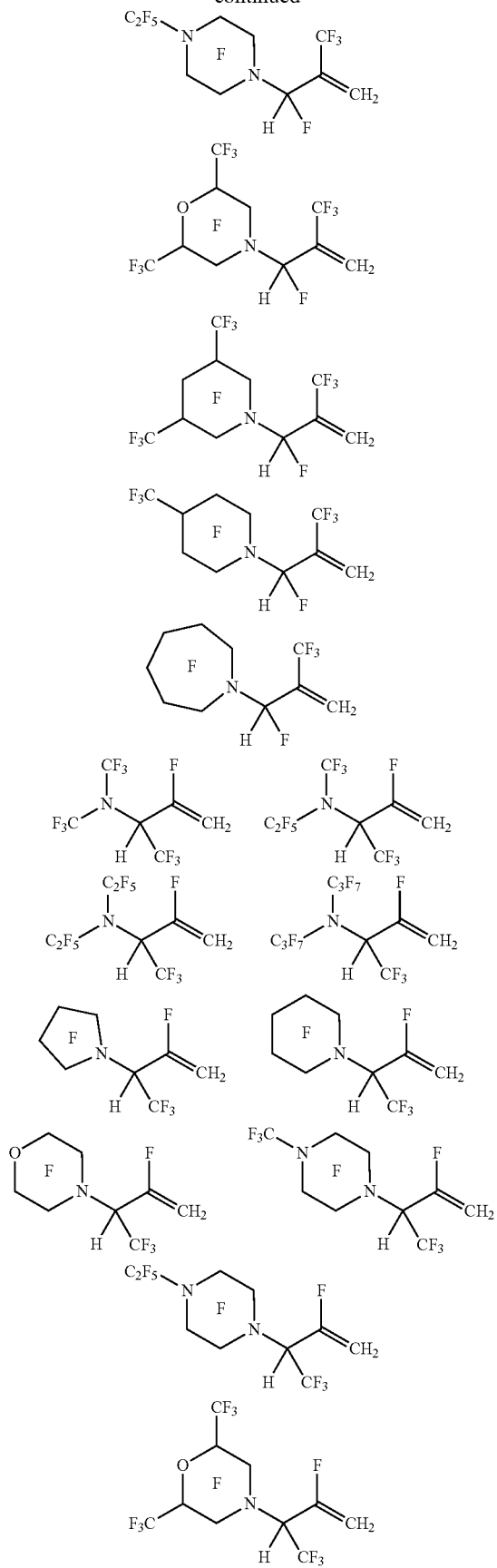
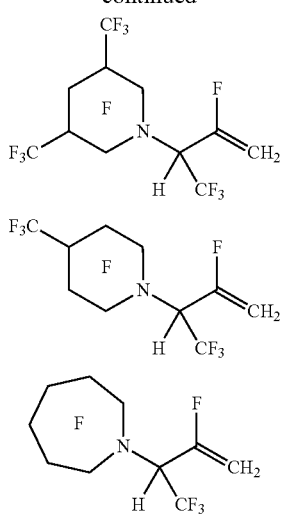
and combinations thereof.
Embodiment 6
The unsaturated fluorinated compound of embodiment 1, wherein the unsaturated fluorinated compound comprises at least one of the following:

-continued
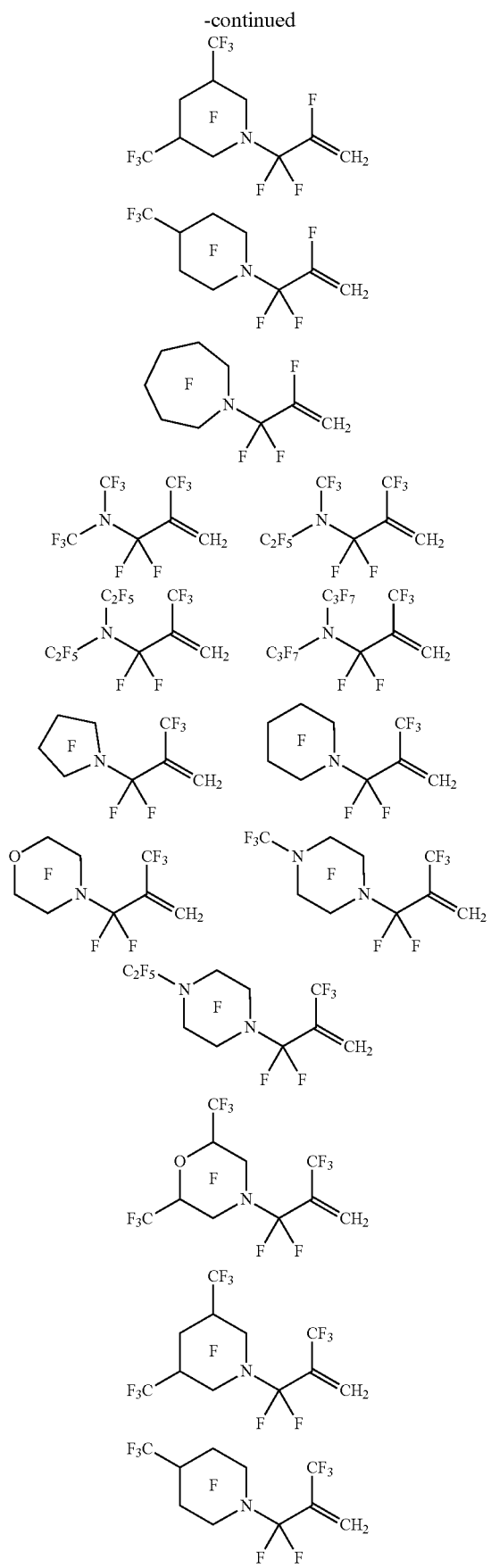
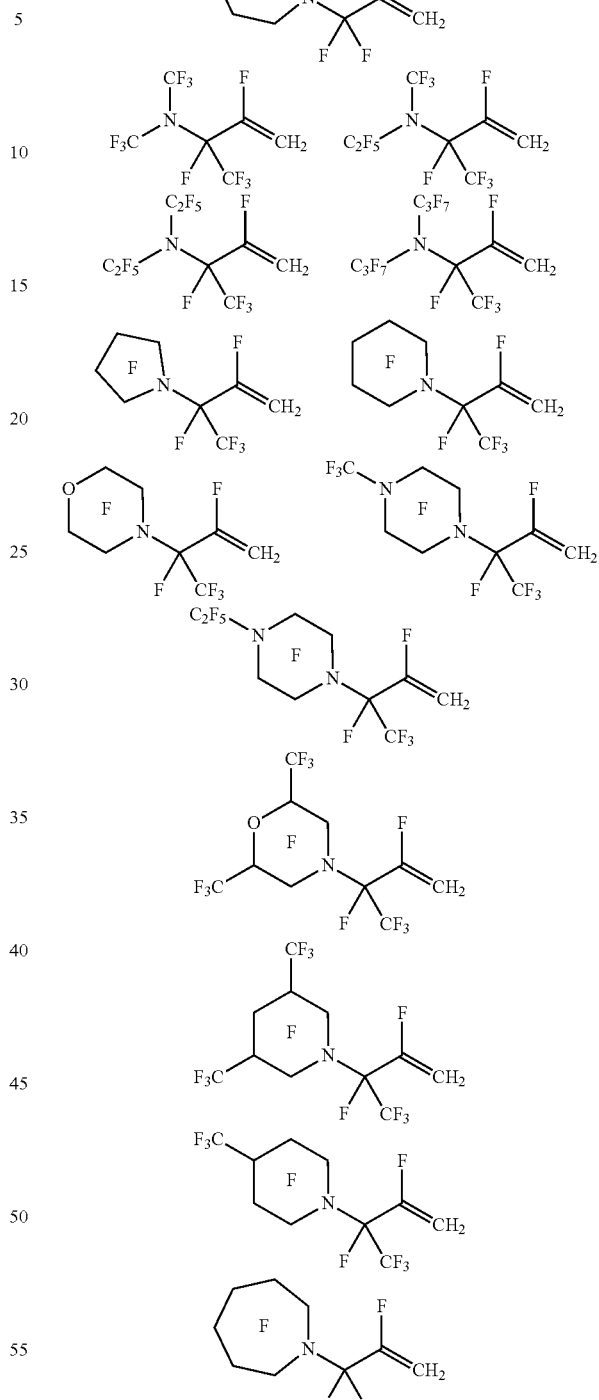
and combinations thereof.
Embodiment 7
The unsaturated fluorinated compound of embodiment 1, wherein the unsaturated fluorinated compound comprises at least one of the following:

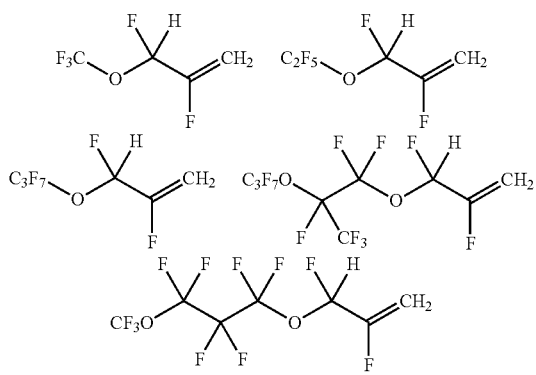

and combinations thereof.

Embodiment 8

The unsaturated fluorinated compound of any one of the previous embodiments, wherein the unsaturated fluorinated compound is nonflammable based on closed-cup flashpoint testing following ASTM D-327-96 e-1.

Embodiment 9

The unsaturated fluorinated compound of any one of the previous embodiments, wherein the unsaturated fluorinated compound has a global warming potential of less than 100.

Embodiment 10

A working fluid comprising the unsaturated fluorinated compound according to any one of the previous embodiments, wherein the unsaturated fluorinated compound is present in the working fluid in an amount of at least 25% by weight based on the total weight of the working fluid.

Embodiment 11

The working fluid of embodiment 10, wherein the working fluid further comprises a co-solvent.

Embodiment 12

Use of the unsaturated fluorinated compound of any one embodiments 1-9, wherein the unsaturated fluorinated compound is in a cleaning composition.

Embodiment 13

Use of the unsaturated fluorinated compound of any one embodiments 1-9, wherein the unsaturated fluorinated compound is an electrolyte solvent or additive.

Embodiment 14

Use of the unsaturated fluorinated compound of any one embodiments 1-9, wherein the unsaturated fluorinated compound is a heat transfer fluid.

Embodiment 15

Use of the unsaturated fluorinated compound of any one embodiments 1-9, wherein the unsaturated fluorinated compound is a fire extinguishing agent.

Embodiment 16

An apparatus for heat transfer comprising:
a device; and
a mechanism for transferring heat to or from the device, the mechanism comprising a heat transfer fluid that comprises the unsaturated fluorinated compound according to any one of embodiments 1-9.

EXAMPLES

Unless otherwise noted, all parts, percentages, ratios, etc. in the examples and the rest of the specification are by weight, and all reagents used in the examples were obtained, or are available, from general chemical suppliers such as, for example, Sigma-Aldrich Company, Saint Louis, Mo., or may be synthesized by conventional methods.

These abbreviations are used in the following examples: mL=milliliter; min=minute; hr=hour; and GC=gas chromatography.

Example 1: Preparation of 4-(1,2-difluoroallyl)-2,2,3,3,5,5,6,6-octafluoromorpholine

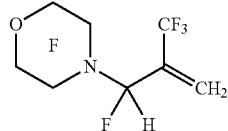

2,2,3,3,5,5,6,6,-Octafluoro-4-(perfluoroprop-1-en-1-yl) morpholine was prepared by electrochemical fluorination/decarboxylation as described in Abe, T.; Hayashi, E. *Chem. Lett.* 1988, 1887-1890. A 600 mL Parr reactor was charged with methanol (70.1 g, 2.19 mol), 2,2,3,3,5,5,6,6,-octafluoro-4-(perfluoroprop-1-en-1-yl)morpholine (74.5 g, 206 mmol), and tert-amylperoxy-2-ethylhexanoate (3.0 g, 13 mmol)). The reactor was then sealed and the mixture was heated (75° C.) and stirred for 16 hours. The temperature was then raised (90° C.) followed by a 30 min stir to consume any remaining initiator. After cooling to room temperature, the mixture was washed with water (100 mL). The fluorous phase was collected and purified by single-plate distillation under reduced pressure (100 torr, 30.6° C. for excess methanol removal; and 2.6 torr, 50.3° C. for desired compound) to afford 2,3,3,3-trifluoro-2-(fluoro(perfluoromorpholino)methyl)propan-1-ol (61.5 g, 76% yield) as a colorless liquid.

To a 3-neck flask equipped with an overhead stir, temperature probe, and water-cooled short-path distillation head under a $N_2$ atmosphere was charged $TiCl_4$ (5.6 mL, 51 mmol). 2,3,3,3-Trifluoro-2-(fluoro(perfluoromorpholino) methyl)propan-1-ol (13.1 g, 33.3 mmol) was added dropwise and the internal temperature was then raised to 40° C. followed by a 30 min stir. The resultant mixture was then cooled to 0° C. followed by the slow addition of tetraethylene glycol dimethyl ether (50 mL) with vigorous stirring. Initial addition resulted in a solidified mixture. Upon complete addition of the tetraethylene glycol dimethyl ether, the mixture returned to liquid form. The reaction mixture was then allowed to rise to room temperature followed by the addition of zinc dust (6.6 g, 100 mmol) in one portion. The resultant mixture was then heated to 85° C. with vigorous stirring. After a 3 hour stir at the same temperature, the reaction mixture was slowly heated to 215° C. with distillate collection beginning at 190° C. reaction temperature. The collected distillate was then re-distilled to give the title compound (3.3 g, 28% yield) as a colorless liquid. GC-MS analysis confirmed the title composition.

Example 2: Preparation of 1,1,-difluoro-N,N,2-tris(trifluoromethyl)prop-2-en-1-amine

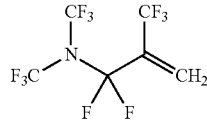

3-(Bis(trifluoromethyl)amino)-2,3,3-trifluoro-2-(trifluoromethyl)propanoyl fluoride was prepared by electrochemical fluorination as described in Abe, T.; Hayashi, E. *Chem. Lett.* 1988, 1887-1890. To a three-neck flask equipped with a water-cooled condenser, addition funnel, and magnetic stir bar was added sodium borohydride (3.0 g, 79 mmol). The flask was evacuated and back-filled with $N_2$ three times followed by the addition of tetraethylene glycol dimethyl ether (50 mL). To the resultant mixture was added 3-(bis(trifluoromethyl)amino)-2,3,3-trifluoro-2-(trifluoromethyl)propanoyl fluoride (25 g, 72 mmol) dropwise via the addition funnel. The resultant mixture was stirred for 16 hours at a heating mantle temperature of 85° C. The reaction mixture temperature was then allowed to cool to room temperature followed by the slow addition of methanol (80 mL) followed by water (50 mL). The fluorous phase was then collected and GC analysis indicated a mixture of product and tetraethylene glycol dimethyl ether. A subsequent water wash (50 mL) afforded 3-(bis(trifluoromethyl)amino)-2,3,3-trifluoro-2-(trifluoromethyl)propan-1-ol (11.4 g, 47.8%) as a colorless liquid.

To a 3-neck flask equipped with an overhead stir, temperature probe, and water-cooled short-path distillation head under an $N_2$ atmosphere was charged $TiCl_4$ (5.6 mL, 51 mmol). 3-(Bis(trifluoromethyl)amino)-2,3,3-trifluoro-2-(trifluoromethyl)propan-1-ol (11.1 g, 33.3 mmol) was added dropwise and the internal temperature was then raised to 40° C. followed by a 30 min stir. The resultant mixture was then cooled to 0° C. followed by the slow addition of tetraethylene glycol dimethyl ether (50 mL) with vigorous stirring. Initial addition resulted in a solidified mixture. Upon complete addition of the tetraethylene glycol dimethyl ether, the mixture returned to liquid form. The reaction mixture was then allowed to rise to room temperature followed by the addition of zinc dust (7.1 g, 100 mmol) in one portion. The resultant mixture was then heated to 85° C. with vigorous stirring. After a 3 hour stir at the same temperature, the reaction mixture was slowly heated to 215° C. with distillate collection beginning at 190° C. reaction temperature. The collected distillate was then re-distilled to give the title compound (5.1 g, 52% yield) as a colorless liquid with a boiling point of 76° C. under ambient pressure. GC-MS analysis confirmed the title composition.

Example 3: Preparation of 2,2,3,3,5,5,6,6-Octafluoro-4-(1,1,1,2,3-pentafluorobut-3-en-2-yl)morpholine

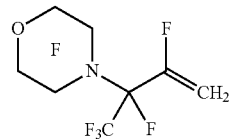

2,2,3,4,4,4-Hexafluoro-3-(perfluoromorpholino)butanoyl fluoride was prepared by electrochemical fluorination as described in Abe, T.; Hayashi, E. *Chem. Lett.* 1988, 1887-1890. The reduction of 2,2,3,4,4,4-hexafluoro-3-(perfluoromorpholino)butanoyl fluoride was carried out as described in Example 2. To a 3-neck flask equipped with an overhead stir, temperature probe, and water-cooled short-path distillation head under an $N_2$ atmosphere was charged $TiCl_4$ (6.1 mL, 55 mmol). 2,2,3,4,4,4-Hexafluoro-3-(perfluoromorpholino)butan-1-ol (15.1 g, 36.7 mmol) was added dropwise and the internal temperature was then raised to 40° C. followed by a 30 min stir. The resultant mixture was then cooled to 0° C. followed by the slow addition of tetraethylene glycol dimethyl ether (50 mL) with vigorous stirring. Initial addition resulted in a solidified mixture. Upon complete addition of the tetraethylene glycol dimethyl ether, the mixture returned to liquid form. The reaction mixture was then allowed to rise to room temperature followed by the addition of zinc dust (7.5 g, 110 mmol) in one portion. The resultant mixture was then heated to 85° C. with vigorous stirring. After a 3 hour stir at the same temperature, the reaction mixture was slowly heated to 225° C. with distillate collection beginning at 205° C. reaction temperature. GC-MS analysis confirmed the title composition.

Example 4: Preparation of 2,3-difluoro-3-(1,1,2,2,3,3-hexafluoro-3-(trifluoromethoxy)propoxy)prop-1-ene

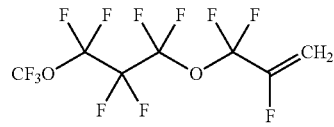

1,1,2,2,3,3-Hexafluoro-1-(trifluoromethoxy)-3-((1,2,2-trifluorovinyl)oxy)propane was prepared by decarboxylation as described in Lebedev, N. V.; Berenblit, V. V.; Starobin, Y. K.; Gubanov, V. A. *Russian J. of Appl. Chem.* 2005, 78, 1640-1645. A 600 mL Parr reactor was charged with methanol (42.5 g, 1.33 mol), 1,1,2,2,3,3-hexafluoro-1-(trifluoromethoxy)-3-((1,2,2-trifluorovinyl)oxy)propane (48.9 g, 147 mmol), and tert-amylperoxy-2-ethylhexanoate (2.0 g, 8.7 mmol). The reactor was then sealed and the mixture was heated (75° C.) and stirred for 16 hours. The temperature was then raised (90° C.) followed by a 30 min stir to consume any remaining initiator. After cooling to room temperature, the mixture was washed with $H_2O$ (100 mL). The fluorous phase was collected and purified by single-plate distillation under reduced pressure (10 torr, 55.6° C.) to afford 2,2,3-trifluoro-3-(1,1,2,2,3,3-hexafluoro-3-(trifluoromethoxy)propoxy)propan-1-ol (42.5 g, 79%) as a colorless liquid.

To a 3-neck flask equipped with an overhead stir, temperature probe, and water-cooled short-path distillation head under an $N_2$ atmosphere was charged $TiCl_4$ (4.8 mL, 44 mmol). 2,2,3-trifluoro-3-(1,1,2,2,3,3-hexafluoro-3-(trifluoromethoxy)propoxy)propan-1-ol (10.1 g, 27.7 mmol) was added dropwise and the internal temperature was then raised to 40° C. followed by a 30 min stir. The resultant mixture was then cooled to 0° C. followed by the slow addition of tetraethylene glycol dimethyl ether (50 mL) with vigorous stirring. Initial addition resulted in the formation of a highly viscous mixture. Upon complete addition of the tetraethylene glycol dimethyl ether, the viscosity of the mixture was significantly attenuated. The reaction mixture was then allowed to rise to room temperature followed by the addition of zinc dust (5.4 g, 83 mmol) in one portion. The resultant mixture was then heated to 85° C. with vigorous stirring. After a 3 hour stir at the same temperature, the reaction mixture was slowly heated to 215° C. with distillate collection beginning at 200° C. reaction temperature. The title composition was confirmed by GC-MS analysis.

Example 5: Preparation of 4-(1,1-difluoro-2-(trifluoromethyl)allyl)-2,2,3,3,5,5,6,6-octafluoromorpholine

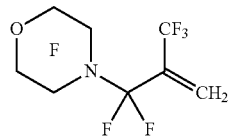

2-(Difluoro(perfluoromorpholino)methyl)-2,3,3,3-tetrafluoropropanoyl fluoride was prepared by electrochemical fluorination as described in Abe, T.; Hayashi, E. *Chem. Lett.* 1988, 1887-1890. To a three-neck flask equipped with a water-cooled condenser, addition funnel, and magnetic stir bar was added sodium borohydride (10.0 g, 263 mmol). The flask was evacuated and back-filled with $N_2$ three times followed by the addition of tetraethylene glycol dimethyl ether (78 mL). To the resultant mixture was added 2-(difluoro(perfluoromorpholino)methyl)-2,3,3,3-tetrafluoropropanoyl fluoride (75 g, 176 mmol) dropwise via the addition funnel. After complete addition, the resultant mixture was stirred for 16 hours at a heating mantle temperature of 85° C. The reaction mixture temperature was then allowed to cool to room temperature followed by the slow addition of methanol (100 mL) followed by water (150 mL). The fluorous phase was then collected and GC analysis indicated a mixture of product, tetraethylene glycol dimethyl ether, and methanol. Single-plate distillation (51.8° C., 1.0 torr) afforded 2-(difluoro(perfluoromorpholino)methyl)-2,3,3,3-tetrafluoropropan-1-ol (42.4 g, 58.7% yield) as a colorless oil which was used in the next step.

To a 3-neck flask equipped with an overhead stir, temperature probe, and water-cooled short-path distillation head under an $N_2$ atmosphere was charged $TiCl_4$ (4.8 mL, 44 mmol). 2-(difluoro(perfluoromorpholino)methyl)-2,3,3,3-tetrafluoropropan-1-ol (12.1 g, 28.3 mmol) was added dropwise and the internal temperature was then raised to 40° C. followed by a 30 min stir. The resultant mixture was then allowed to cool to room temperature followed by the slow addition of tetraethylene glycol dimethyl ether (45 mL) with vigorous stirring. Initial addition resulted in the formation of a highly viscous mixture. Upon complete addition of the tetraethylene glycol dimethyl ether, the viscosity of the mixture was significantly attenuated. Zinc dust (5.6 g, 86 mmol) was then charged to the mixture followed by a 3 hour stir at 85° C. The reaction mixture was then slowly heated to 225° C. to distill the desired compound from the reaction mixture affording the title compound (3.9 g, 35% yield) as a colorless liquid with a boiling point of 105° C. under ambient pressure. The title composition was confirmed by GC-MS analysis.

Example 6: Preparation of 2,2,3,3,5,5,6,6-octafluoro-1-(1-fluoro-2-(trifluoromethyl)allyl)-4-(perfluoroethyl)piperazine

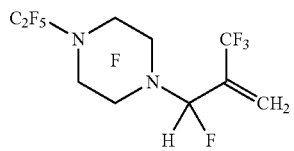

2,2,3,3,5,5,6,6-Octafluoro-1-(perfluoroethyl)-4-(perfluoroprop-1-en-1-yl)piperazine was prepared by electrochemical fluorination/decarboxylation as described in Abe, T.; Hayashi, E. *Chem. Lett.* 1988, 1887-1890. A 600 mL Parr reactor was charged with methanol (55 g, 1.72 mol), 2,2,3,3,5,5,6,6-octafluoro-1-(perfluoroethyl)-4-(perfluoroprop-1-en-1-yl)piperazine (50.5 g, 106 mmol), and tert-butyl peroxide (2.1 g, 14 mmol). The reactor was then sealed and the mixture was heated (125° C.) and stirred for 16 hours. The temperature was then raised (160° C.) followed by a 30 min stir to consume any remaining initiator. After cooling to room temperature, the mixture was washed with $H_2O$ (100 mL). The fluorous phase was collected and purified by single-plate distillation under reduced pressure (70.8° C., 3.0 torr) to afford 2,3,3,3-tetrafluoro-2-(fluoro(2,2,3,3,5,5,6,6-octafluoro-4-(perfluoroethyl)piperazin-1-yl)methyl)propan-1-ol (40.2 g, 75% yield) as a colorless oil which was used in the next step.

To a 3-neck flask equipped with an overhead stir, temperature probe, and water-cooled short-path distillation head under an $N_2$ atmosphere was charged $TiCl_4$ (4.3 mL, 39 mmol). 2,3,3,3-tetrafluoro-2-(fluoro(2,2,3,3,5,5,6,6-octafluoro-4-(perfluoroethyl)piperazin-1-yl)methyl)propan-1-ol (12.1 g, 23.0 mmol) was added dropwise and the internal temperature was then raised to 40° C. followed by a 30 min stir. The resultant mixture was then allowed to cool to room temperature followed by the slow addition of tetraethylene glycol dimethyl ether (45 mL) with vigorous stirring. Initial addition resulted in the formation of a highly viscous mixture. Upon complete addition of the tetraethylene glycol dimethyl ether, the viscosity of the mixture was significantly attenuated. Zinc dust (5.1 g, 78 mmol) was then charged to the mixture followed by a 3 hour stir at 85° C. The reaction mixture was then slowly heated to 230° C. to distill the desired compound from the reaction mixture. GC-MS analysis of the distillate confirmed formation of the title compound.

Example 7: Preparation of 2,2,3,3,5,5,6,6-octafluoro-4-(1,1,1,3-tetrafluorobut-3-en-2-yl)morpholine

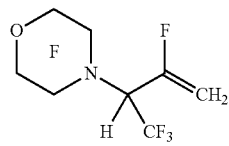

2,2,3,3,5,5,6,6-Octafluoro-4-(perfluoroprop-1-en-2-yl)morpholine was prepared by electrochemical fluorination/decarboxylation as described in Abe, T.; Hayashi, E. *Chem. Lett.* 1988, 1887-1890. A 600 mL Parr reactor was charged with trimethoxyborate (35.9 g, 345 mmol), 2,2,3,3,5,5,6,6-octafluoro-4-(perfluoroprop-1-en-2-yl)morpholine (40.5 g, 112 mmol), and tert-amylperoxy-2-ethylhexanoate (4.2 g, 18 mmol). The reactor was then sealed and the mixture was heated (75° C.) and stirred for 16 hours. The temperature was then raised (90° C.) followed by a 30 min stir to consume any remaining initiator. The reaction mixture was allowed to cool to room temperature followed by the slow addition of $H_2O$ (100 mL) to convert the afforded fluorinated borate species the desired fluorinated alcohol. The fluorous phase was collected and purified by single-plate distillation under reduced pressure (49.7° C., 3.0 torr) to afford 1,1,3,3,3-pentafluoro-2-(perfluoromorpholino)propan-1-ol (32 g, 73% yield) as a colorless oil which was used in the next step.

To a 3-neck flask equipped with an overhead stir, temperature probe, and water-cooled short-path distillation head under an $N_2$ atmosphere was charged $TiCl_4$ (5.0 mL, 45 mmol). 1,1,3,3,3-pentafluoro-2-(perfluoromorpholino)propan-1-ol (12.1 g, 29.6 mmol) was added dropwise and the internal temperature was then raised to 40° C. followed by a 30 min stir. The resultant mixture was then allowed to cool to room temperature followed by the slow addition of tetraethylene glycol dimethyl ether (45 mL) with vigorous stirring. Initial addition resulted in the formation of a highly viscous mixture. Upon complete addition of the tetraethylene glycol dimethyl ether, the viscosity of the mixture was significantly attenuated. Zinc dust (6.2 g, 95 mmol) was then charged to the mixture followed by a 3 hour stir at 85° C. The reaction mixture was then slowly heated to 225° C. to distill the desired compound from the reaction mixture. GC-MS analysis of the distillate confirmed formation of the title compound.

Example 8: Preparation of 2,2,3,3,4,4,5,5-octafluoro-1-(1,1,2-trifluoroallyl)pyrrolidine

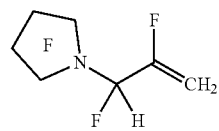

2,2,3,3-Tetrafluoro-3-(perfluoropyrrolidin-1-yl)propanoyl fluoride was prepared by electrochemical fluorination as described in Abe, T.; Hayashi, E. *Chem. Lett.* 1988, 1887-1890. To a three-neck flask equipped with a water-cooled condenser, addition funnel, and magnetic stir bar was added sodium borohydride (15.7 g, 415 mmol). The flask was evacuated and back-filled with $N_2$ three times followed by the addition of tetraethylene glycol dimethyl ether (125 g). To the resultant mixture was added 2,2,3,3-tetrafluoro-3-(perfluoropyrrolidin-1-yl)propanoyl fluoride (100 g, 277 mmol) dropwise via the addition funnel. The resultant mixture was stirred for 16 hours at a heating mantle temperature of 85° C. The reaction mixture temperature was then allowed to cool to room temperature followed by the slow addition of methanol (100 mL) followed by the slow addition of $H_2O$ (150 mL). The fluorous phase was then collected and GC analysis indicated a mixture of product, tetraethylene glycol dimethyl ether, and methanol. Single-plate distillation under reduced pressure (54.6° C., 0.3 torr) afforded 2,2,3,3-tetrafluoro-3-(perfluoropyrrolidin-1-yl)propan-1-ol (63.9 g, 70% yield) as a colorless oil which was used in the next step.

To a 3-neck flask equipped with an overhead stir, temperature probe, and water-cooled short-path distillation head under an $N_2$ atmosphere was charged $TiCl_4$ (7.2 mL, 65 mmol). 2,2,3,3-tetrafluoro-3-(perfluoropyrrolidin-1-yl)propan-1-ol (15.1 g, 43.8 mmol) was added dropwise and the internal temperature was then raised to 40° C. followed by a 30 min stir. The resultant mixture was then allowed to cool to room temperature followed by the slow addition of tetraethylene glycol dimethyl ether (45 mL) with vigorous stirring. Initial addition resulted in the formation of a highly viscous mixture. Upon complete addition of the tetraethylene glycol dimethyl ether, the viscosity of the mixture was significantly attenuated. Zinc dust (8.3 g, 130 mmol) was then charged to the mixture followed by a 3 hour stir at 85° C. The reaction mixture was then slowly heated to 225° C. to distill the desired compound from the reaction mixture. GC-MS analysis of the distillate confirmed formation of the title compound.

Foreseeable modifications and alterations of this invention will be apparent to those skilled in the art without departing from the scope and spirit of this invention. This invention should not be restricted to the embodiments that are set forth in this application for illustrative purposes.

What is claimed is:
1. An unsaturated fluorinated compound of formula (I):

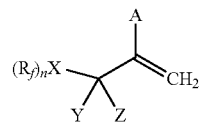

where X is N;
Y is F or H;
Z is F or $CF_3$;
A is F or $CF_3$;
n is 2; and
each $R_f$ group is (i) independently selected from a linear or branched perfluorinated alkyl group comprising 1 to 8 carbon atoms and optionally comprising at least one catenated O or N atom; or (ii) bonded together to form a ring structure comprising 4 to 8 carbon atoms and optionally comprising at least one catenated O or N atom with the proviso that when Z is $CF_3$ then A is F and when A is $CF_3$ then Z is F.

2. The unsaturated fluorinated compound of claim 1, wherein Y is F.

3. The unsaturated fluorinated compound of claim 1, wherein A is F.

4. The unsaturated fluorinated compound of claim 1, wherein the unsaturated fluorinated compound has a percent fluorine content of 75%.
5. The unsaturated fluorinated compound of claim 1, wherein the unsaturated fluorinated compound is selected from the group consisting of:
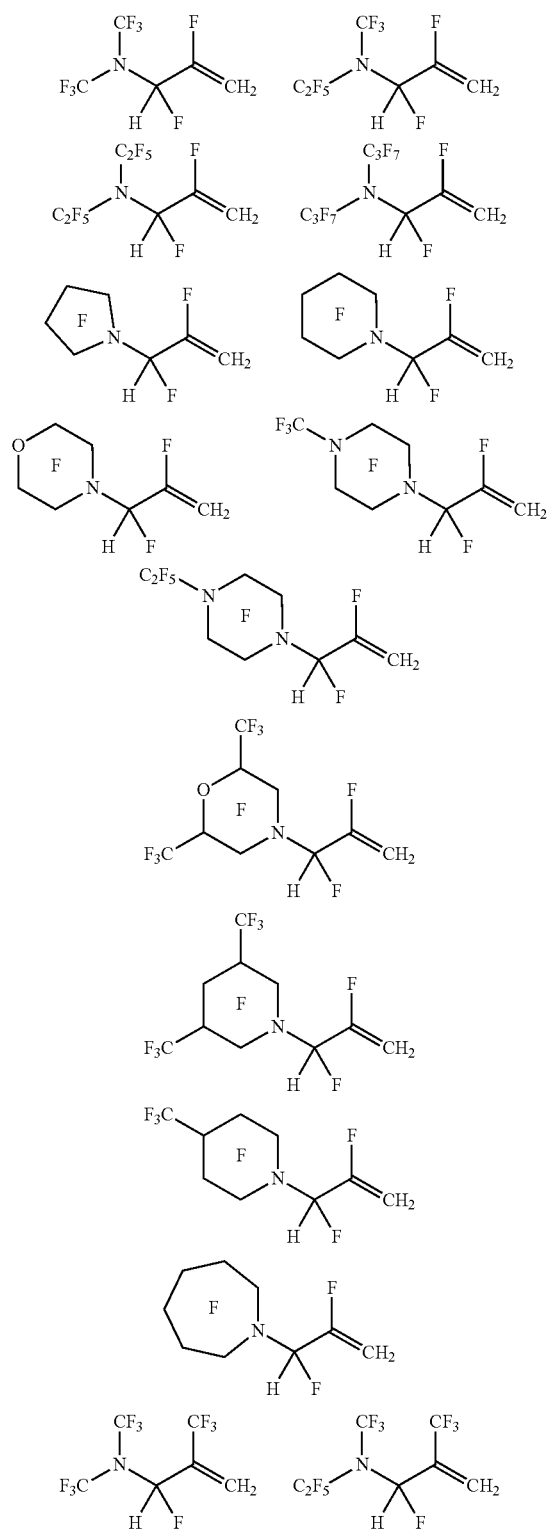
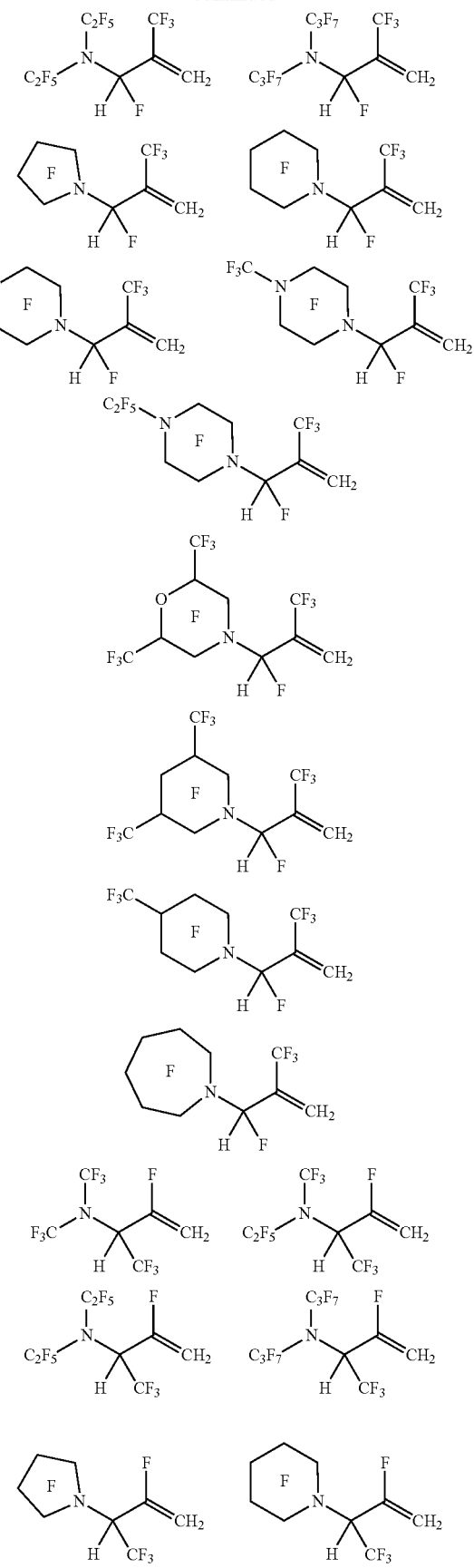

-continued
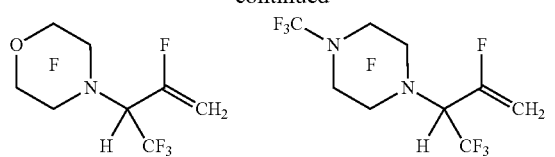
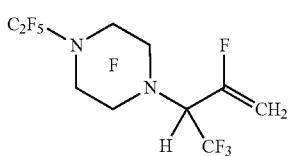
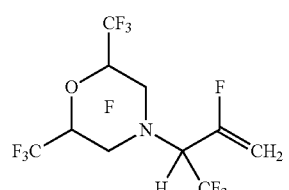
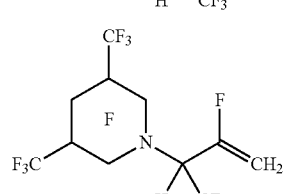
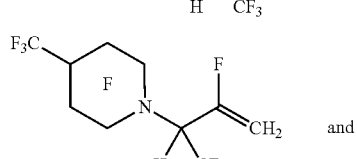
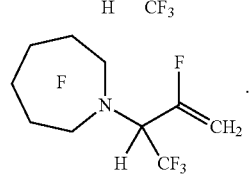 and
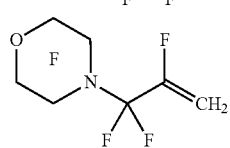
6. The unsaturated fluorinated compound of claim 1, wherein the unsaturated fluorinated compound is selected from the group consisting of:
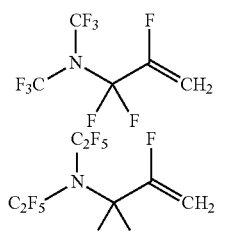
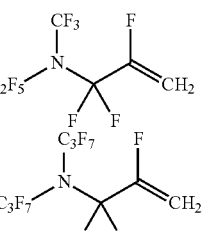
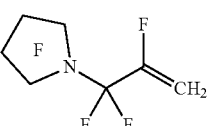
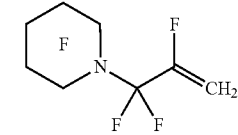
-continued
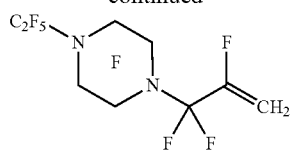
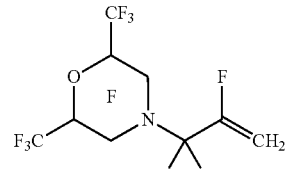
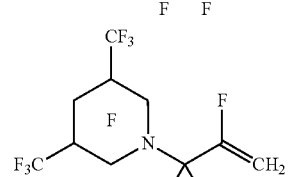
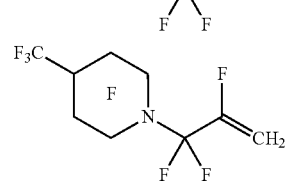
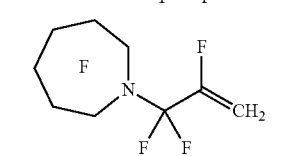
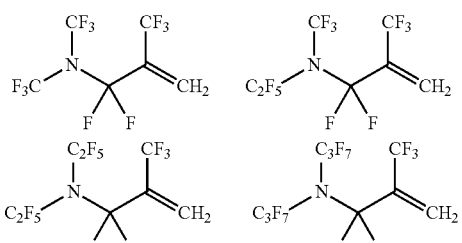
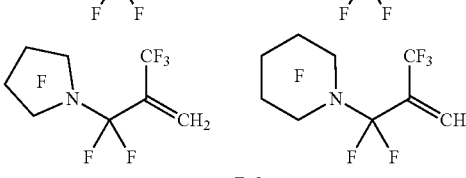
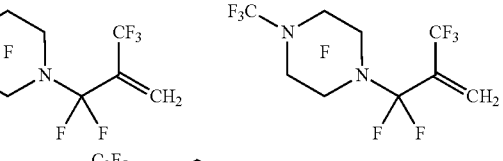
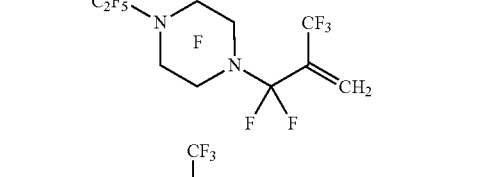
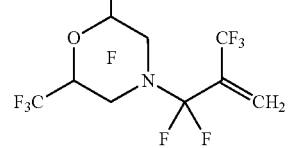

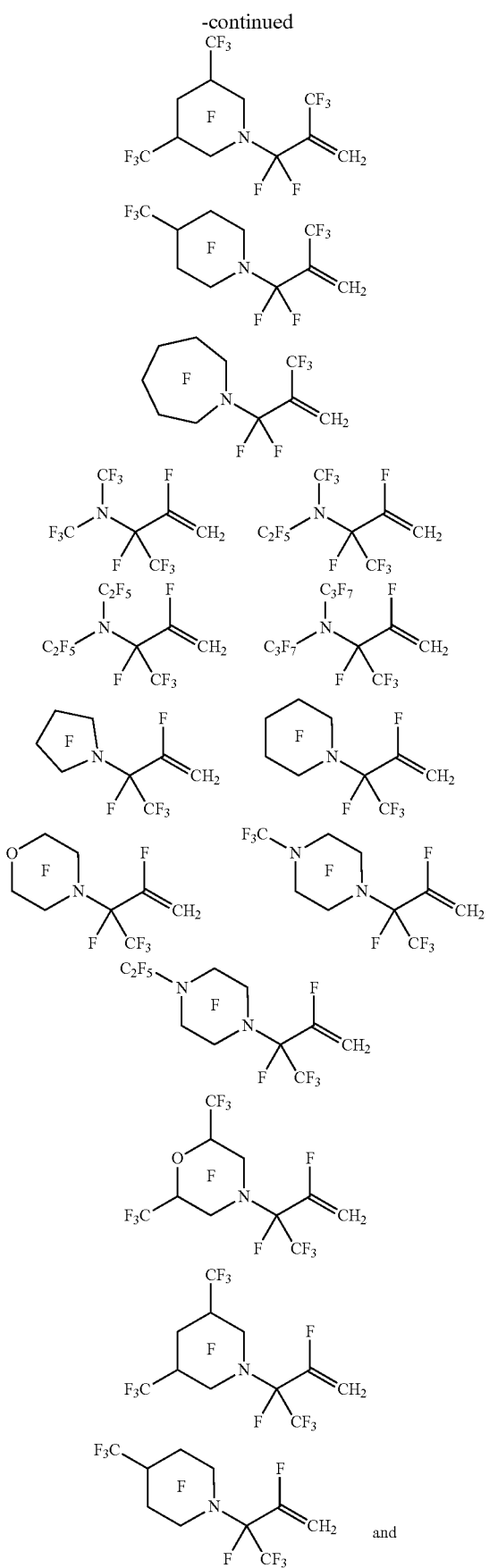

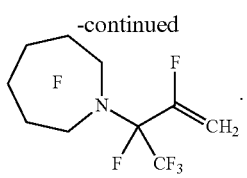

7. An unsaturated fluorinated compound of formula (I):

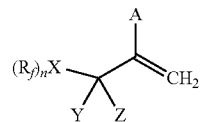

where X is O;
Y is H;
Z is F;
A is F;
n is 1; and
$R_f$ is a linear or branched perfluorinated alkyl group comprising 1 to 10 carbon atoms and optionally comprising at least one catenated O or N atom.

8. A working fluid comprising the unsaturated fluorinated compound according to claim 1, wherein the unsaturated fluorinated compound is present in the working fluid in an amount of at least 25% by weight based on the total weight of the working fluid.

9. A cleaning composition comprising the unsaturated fluorinated compound of claim 1.

10. An electrolyte comprising an electrolyte solvent or additive comprising the unsaturated fluorinated compound of claim 1.

11. A heat transfer fluid comprising the unsaturated fluorinated compound of claim 1.

12. A fire extinguishing agent comprising the unsaturated fluorinated compound of claim 1.

13. The unsaturated fluorinated compound of claim 1, wherein the unsaturated fluorinated compound is nonflammable based on closed-cup flashpoint testing following ASTM D-327-96 e-1 standard test method.

14. The unsaturated fluorinated compound of claim 1, wherein the unsaturated fluorinated compound has a global warming potential of less than 100.

15. The working fluid of claim 8, wherein the working fluid further comprises a co-solvent.

16. The unsaturated fluorinated compound of claim 7, wherein the unsaturated fluorinated compound is selected from the group consisting of:

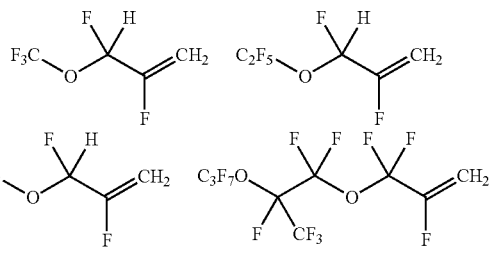

and

-continued
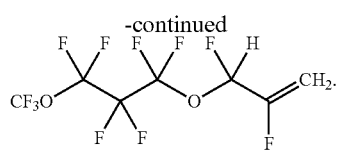
* * * * *

UNITED STATES PATENT AND TRADEMARK OFFICE
CERTIFICATE OF CORRECTION

PATENT NO. : 10,577,335 B2
APPLICATION NO. : 15/770289
DATED : March 3, 2020
INVENTOR(S) : Sean Smith et al.

Page 1 of 1

It is certified that error appears in the above-identified patent and that said Letters Patent is hereby corrected as shown below:

In the Specification

Column 8
Line 62, Delete "N-methylpyrolidone," and insert -- N-methylpyrrolidone, --, therefor.
Line 64, Delete "N-methylepyridine," and insert -- N-methylpyridine, --, therefor.

Column 14
Line 54, Delete "prefluorinated" and insert -- perfluorinated --, therefor.

Column 20
Line 13, Delete "chlorofluorolefins," and insert -- chlorofluoroolefins, --, therefor.
Line 48, After "may" insert -- be --.

Column 25
Line 45, Delete "ClO$_4^-$;" and insert -- ClO$_4^-$; --, therefor.

Column 26
Line 58, Delete "e. g.," and insert -- e.g., --, therefor.
Line 61, Delete "(e. g.," and insert -- (e.g., --, therefor.
Line 62, Delete "Li$_{4/3}$Ti$_{5/3}$0$_4$" and insert -- Li$_{4/3}$Ti$_{5/3}$O$_4$ --, therefor.

Column 27
Line 1, Delete "e. g.," and insert -- e.g., --, therefor.

Signed and Sealed this
Fifth Day of May, 2020

Andrei Iancu
*Director of the United States Patent and Trademark Office*